(12) United States Patent  
Tuli

(10) Patent No.: US 12,115,049 B2  
(45) Date of Patent: Oct. 15, 2024

(54) INCONTINENCE DETECTION SYSTEM

(71) Applicant: Raja Singh Tuli, Montreal (CA)

(72) Inventor: Raja Singh Tuli, Montreal (CA)

( * ) Notice: Subject to any disclaimer, the term of this patent is extended or adjusted under 35 U.S.C. 154(b) by 433 days.

(21) Appl. No.: 16/835,543

(22) Filed: Mar. 31, 2020

(65) Prior Publication Data

US 2020/0306100 A1     Oct. 1, 2020

Related U.S. Application Data

(60) Provisional application No. 62/931,488, filed on Nov. 6, 2019, provisional application No. 62/827,678, filed on Apr. 1, 2019.

(51) Int. Cl.
*A61F 13/42*     (2006.01)
*A61F 13/49*     (2006.01)

(52) U.S. Cl.
CPC .............. *A61F 13/42* (2013.01); *A61F 13/49* (2013.01); *A61F 2013/424* (2013.01); *A61F 2013/428* (2013.01); *A61F 2013/49098* (2013.01)

(58) Field of Classification Search
CPC .... A61F 13/42; A61F 13/49; A61F 2013/424; A61F 2013/428; A61F 2013/49098
See application file for complete search history.

(56) References Cited

U.S. PATENT DOCUMENTS

| | | | | |
|---|---|---|---|---|
| 5,291,181 A | * | 3/1994 | DePonte | A61F 13/42 340/573.6 |
| 5,370,671 A | * | 12/1994 | Maurer | A61N 1/0524 607/138 |
| 5,760,694 A | * | 6/1998 | Nissim | A61F 13/42 128/885 |
| 5,790,035 A | * | 8/1998 | Ho | G08B 21/20 340/573.5 |
| 5,808,554 A | * | 9/1998 | Shuminov | A61F 13/42 604/361 |
| 5,908,411 A | * | 6/1999 | Matsunari | A61F 13/42 604/361 |
| 6,097,297 A | * | 8/2000 | Fard | A61F 13/42 340/573.5 |
| 6,583,722 B2 | * | 6/2003 | Jeutter | A61F 13/42 340/941 |

(Continued)

FOREIGN PATENT DOCUMENTS

| | | | |
|---|---|---|---|
| CN | 112741728 A | * | 5/2021 |
| EP | 3391863 A1 | * | 10/2018 |

(Continued)

*Primary Examiner* — Chico A Foxx

(57) ABSTRACT

"Incontinence detection system" is the title of our invention, described herein, which is designed to work along with any commercially available brief, for people having incontinence issues. The purpose of this complete incontinence management system is to provide a cost-effective solution by using sensor technology that automatically alerts caregivers to change the residents' diapers at precisely the right time. It uses a sensing system that wirelessly transmits individual wetness alerts to an application on a remote device. The system is ready for immediate use when detached from the soaked diaper, and brief changes are made at appropriate times offering the highest level of care to residents. The Pod allows for faster service delivery, less time spent in a wet brief, bringing great relief to residents and caregivers alike.

13 Claims, 34 Drawing Sheets

(56) References Cited

U.S. PATENT DOCUMENTS

| | | | | |
|---|---|---|---|---|
| 7,295,125 B2* | 11/2007 | Gabriel | ............... | A61F 13/42 200/182 |
| 8,866,624 B2* | 10/2014 | Ales, III | ............... | A61F 13/42 340/532 |
| 10,159,607 B2* | 12/2018 | Monson | ............... | G06K 7/10356 |
| 10,716,715 B2* | 7/2020 | Severns | ............... | H01Q 21/08 |
| 11,291,591 B1* | 4/2022 | Gu | ............... | B33Y 80/00 |
| 2012/0150138 A1* | 6/2012 | Endo | ............... | A61F 13/72 604/396 |
| 2013/0018231 A1* | 1/2013 | Hong | ............... | A61F 13/42 600/300 |
| 2013/0018340 A1* | 1/2013 | Abraham | ............... | A61F 13/42 604/361 |
| 2013/0324955 A1* | 12/2013 | Wong | ............... | A61F 13/42 604/361 |
| 2014/0266736 A1* | 9/2014 | Cretu-Petra | ............... | A61B 5/6808 340/573.5 |
| 2015/0164703 A1* | 6/2015 | Bae | ............... | A61F 13/42 324/693 |
| 2015/0257942 A1* | 9/2015 | Kim | ............... | G08B 25/10 604/361 |
| 2017/0258643 A1* | 9/2017 | Xu | ............... | A61F 13/42 |
| 2018/0104115 A1* | 4/2018 | Collette | ............... | A61F 13/42 |
| 2018/0325743 A1* | 11/2018 | Ho | ............... | A61F 13/42 |
| 2019/0038478 A1* | 2/2019 | Lai | ............... | A61B 5/6808 |
| 2020/0196933 A1* | 6/2020 | Van Keymeulen | .... | A61B 5/002 |
| 2021/0100506 A1* | 4/2021 | Baek | ............... | A61B 5/0015 |
| 2021/0100694 A1* | 4/2021 | Baek | ............... | A61F 13/49 |
| 2022/0096279 A1* | 3/2022 | Kurt | ............... | A61F 13/53 |

FOREIGN PATENT DOCUMENTS

| | | | | |
|---|---|---|---|---|
| ES | 2510547 T3 | * | 10/2014 | ......... B01D 53/0423 |
| WO | WO-2004021944 A1 | * | 3/2004 | ............. A61B 5/145 |
| WO | WO-2013187742 A1 | * | 12/2013 | ............. A61F 13/42 |
| WO | WO-2020245315 A1 | * | 12/2020 | ............. A61F 13/42 |

* cited by examiner

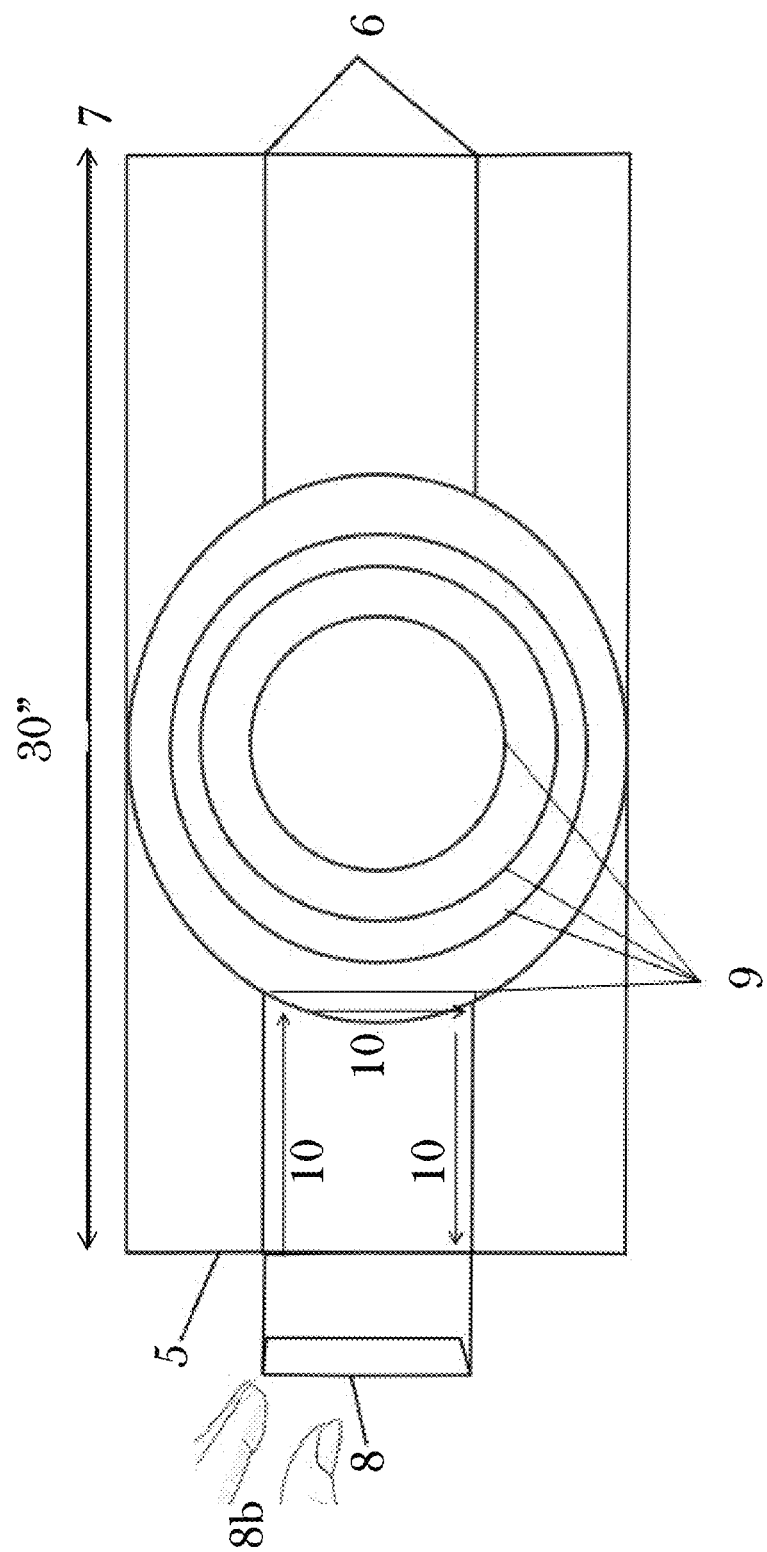

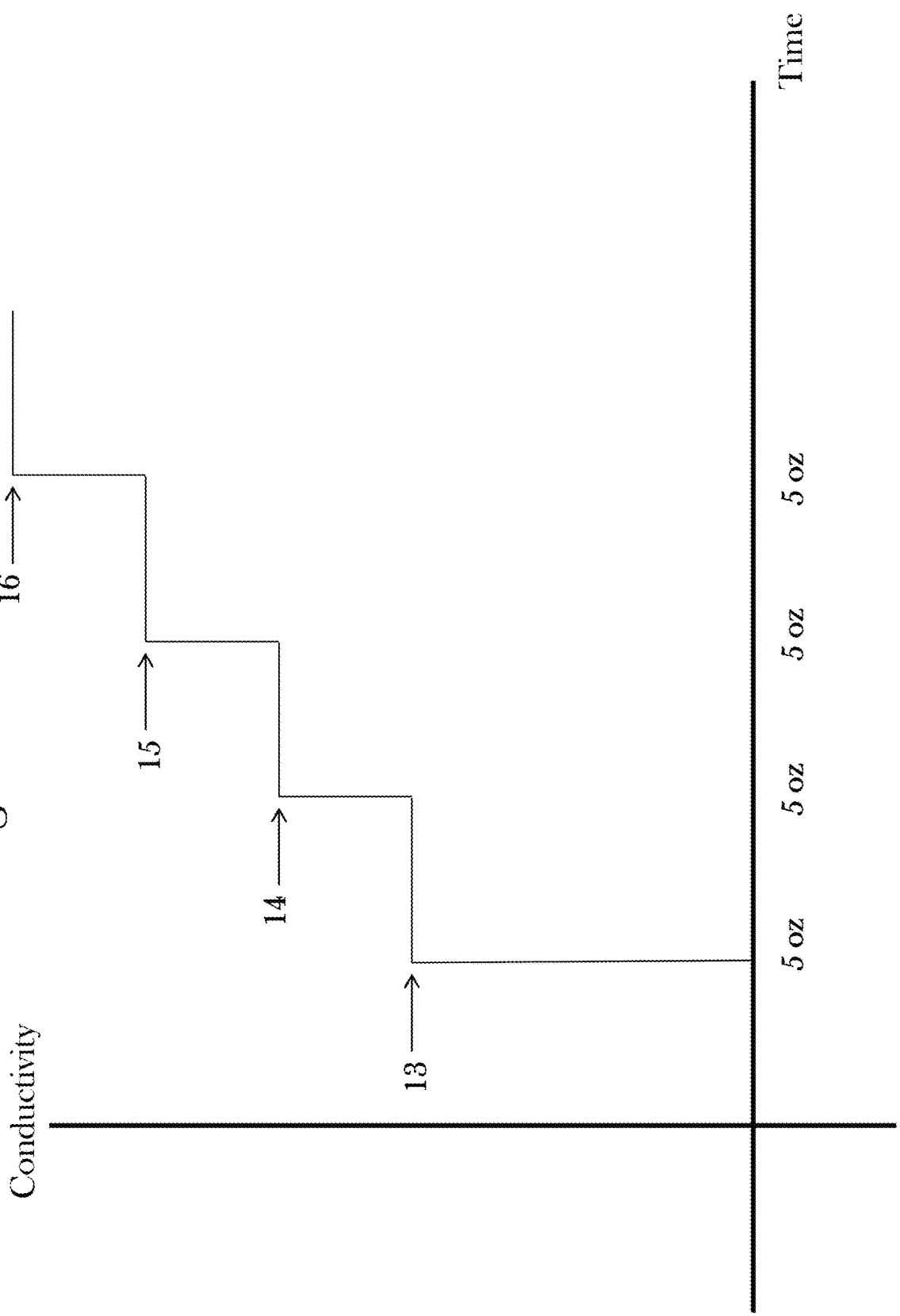

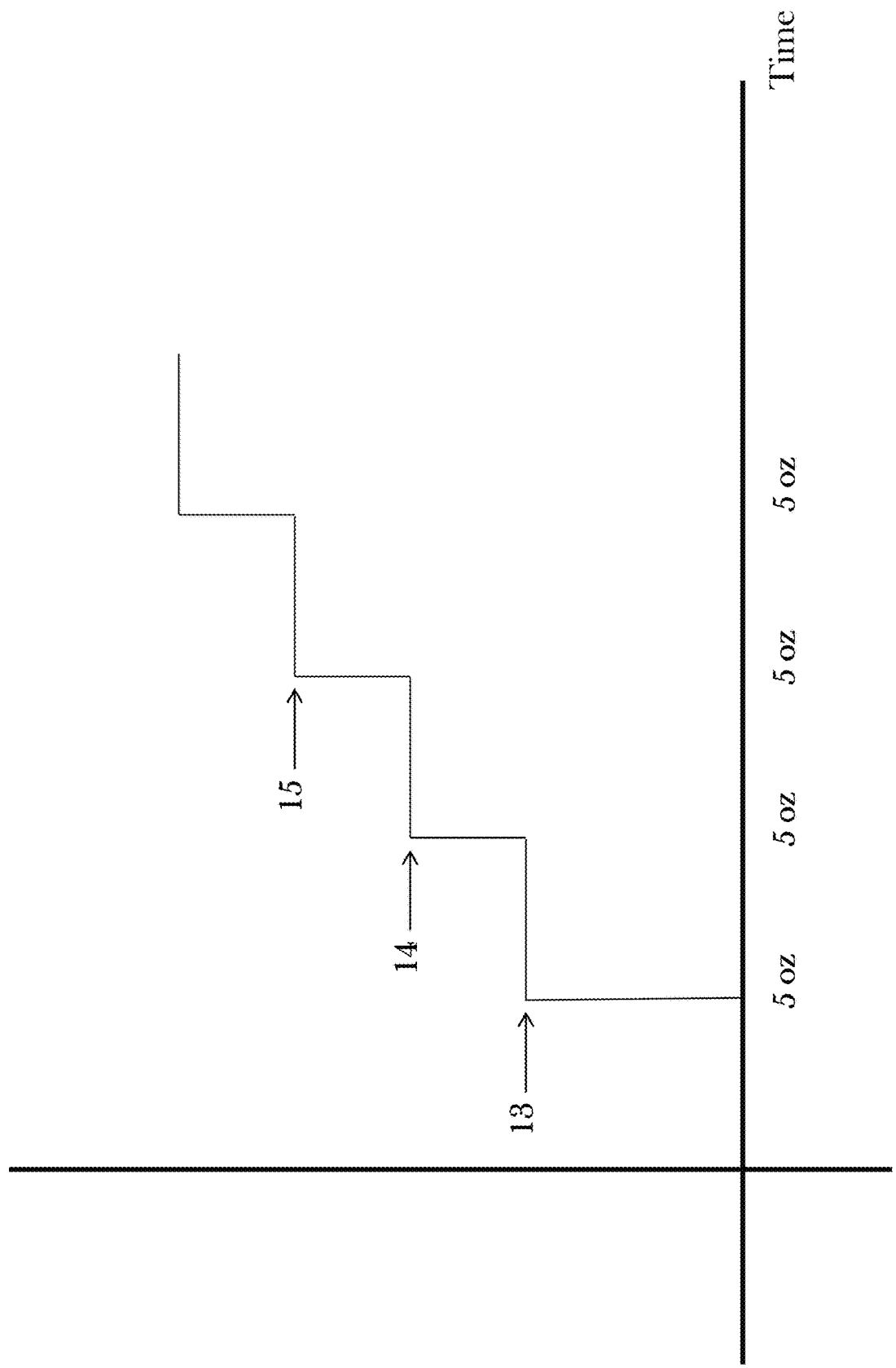

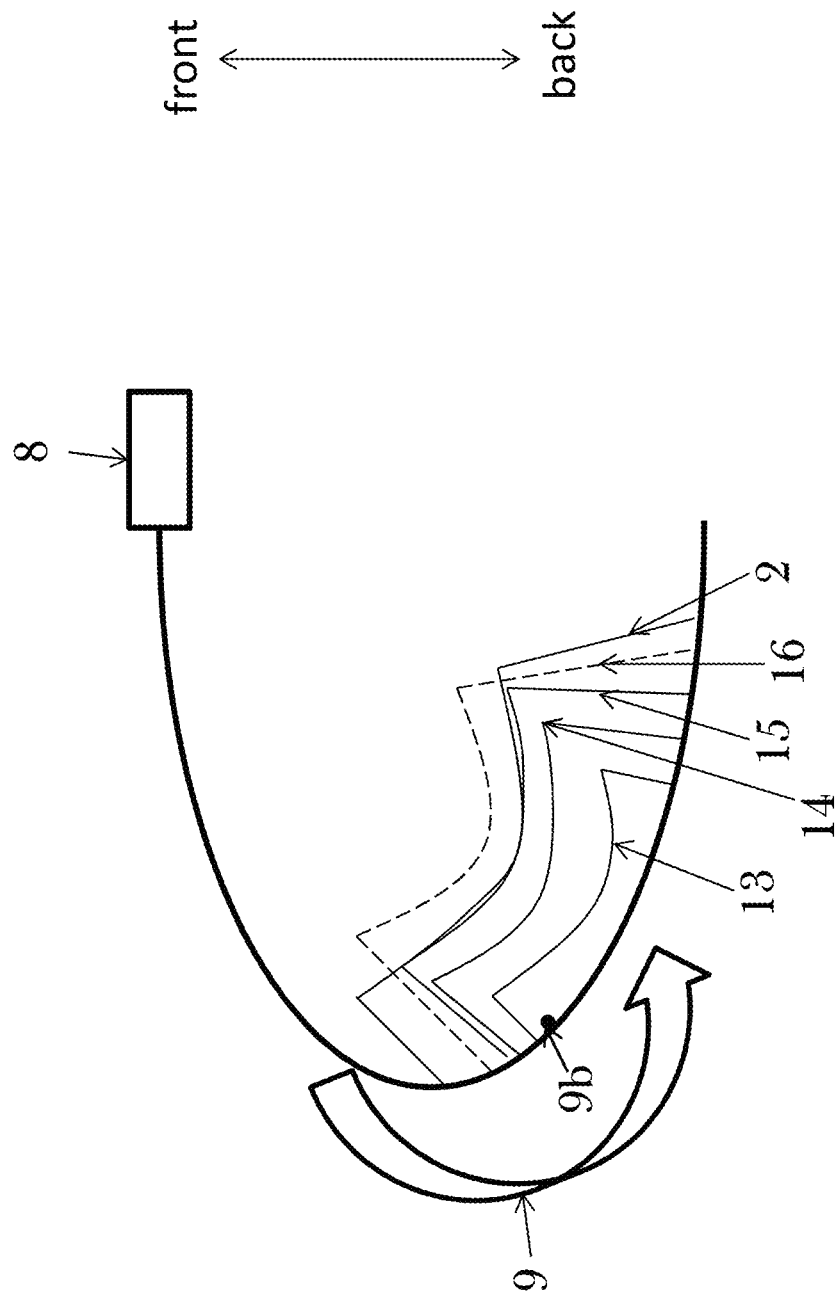

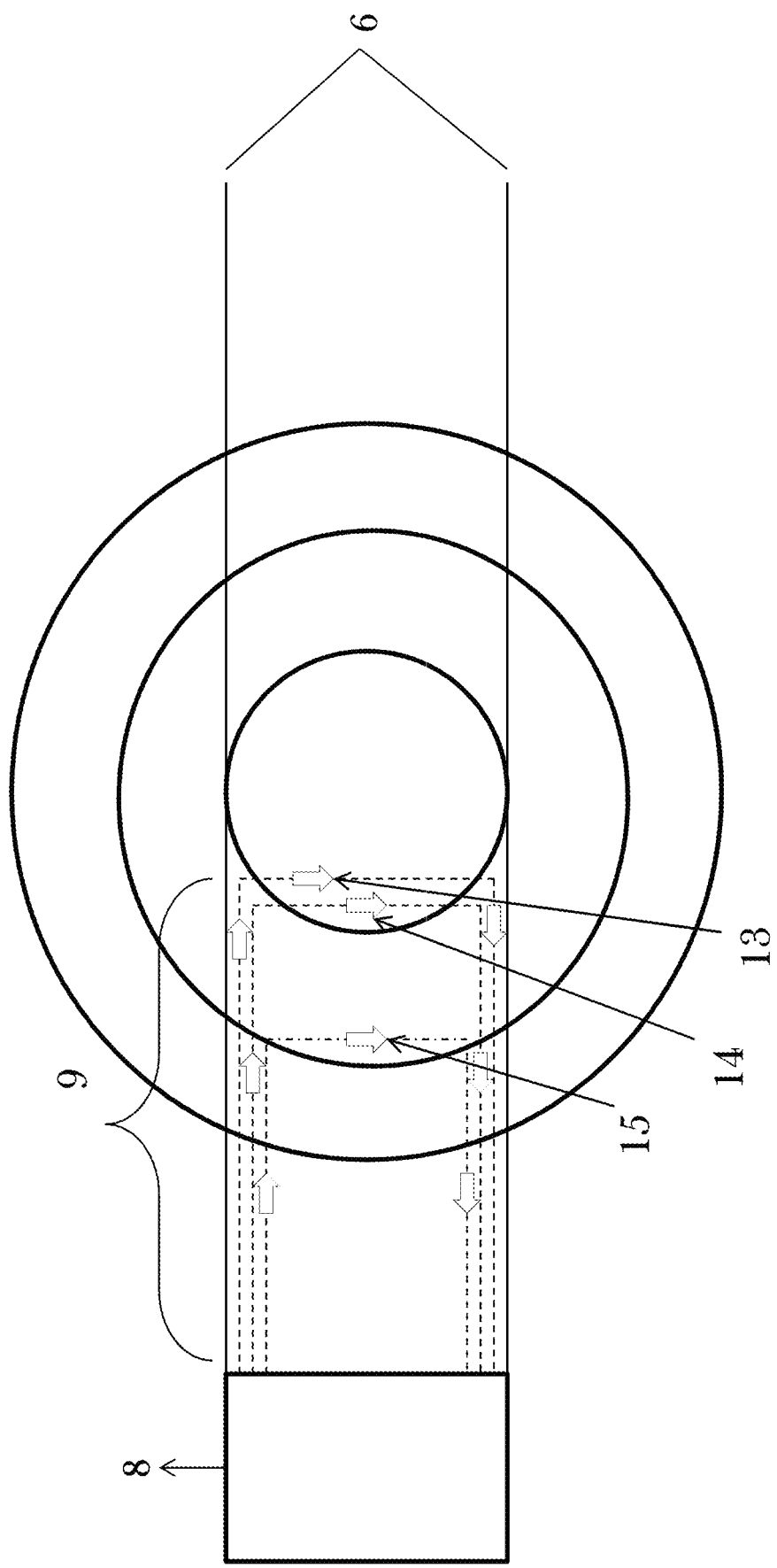

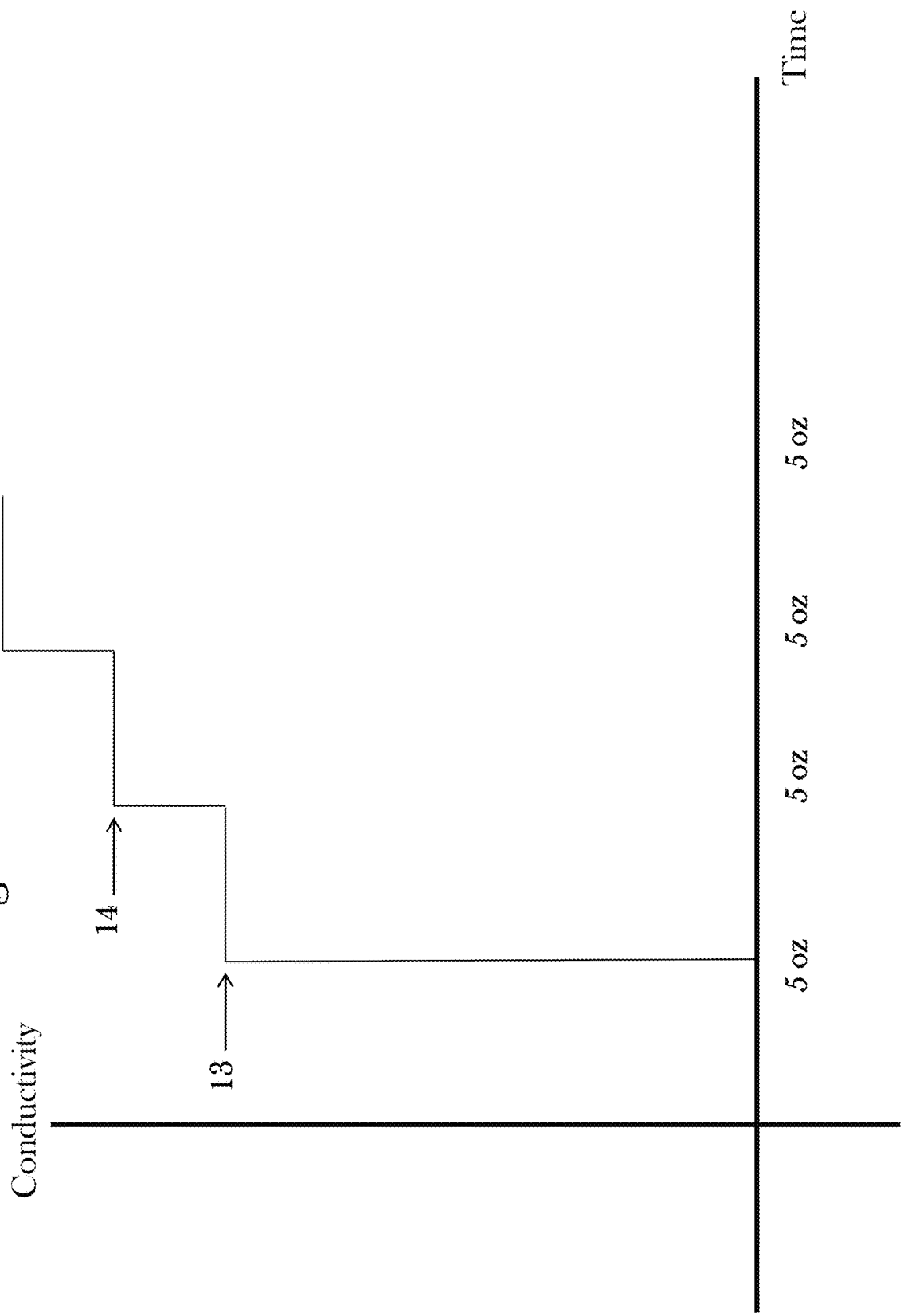

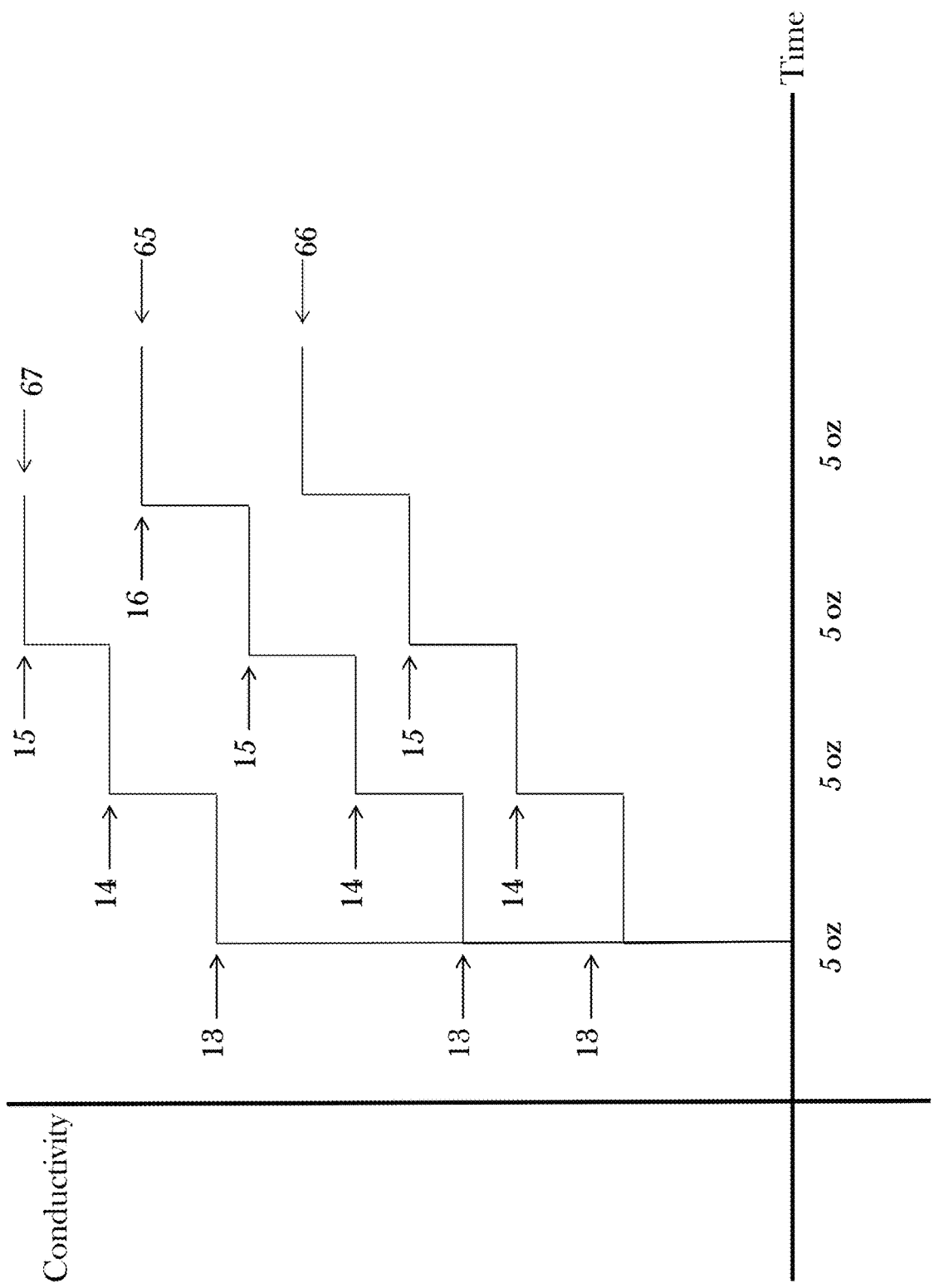
Figure 6 B.5

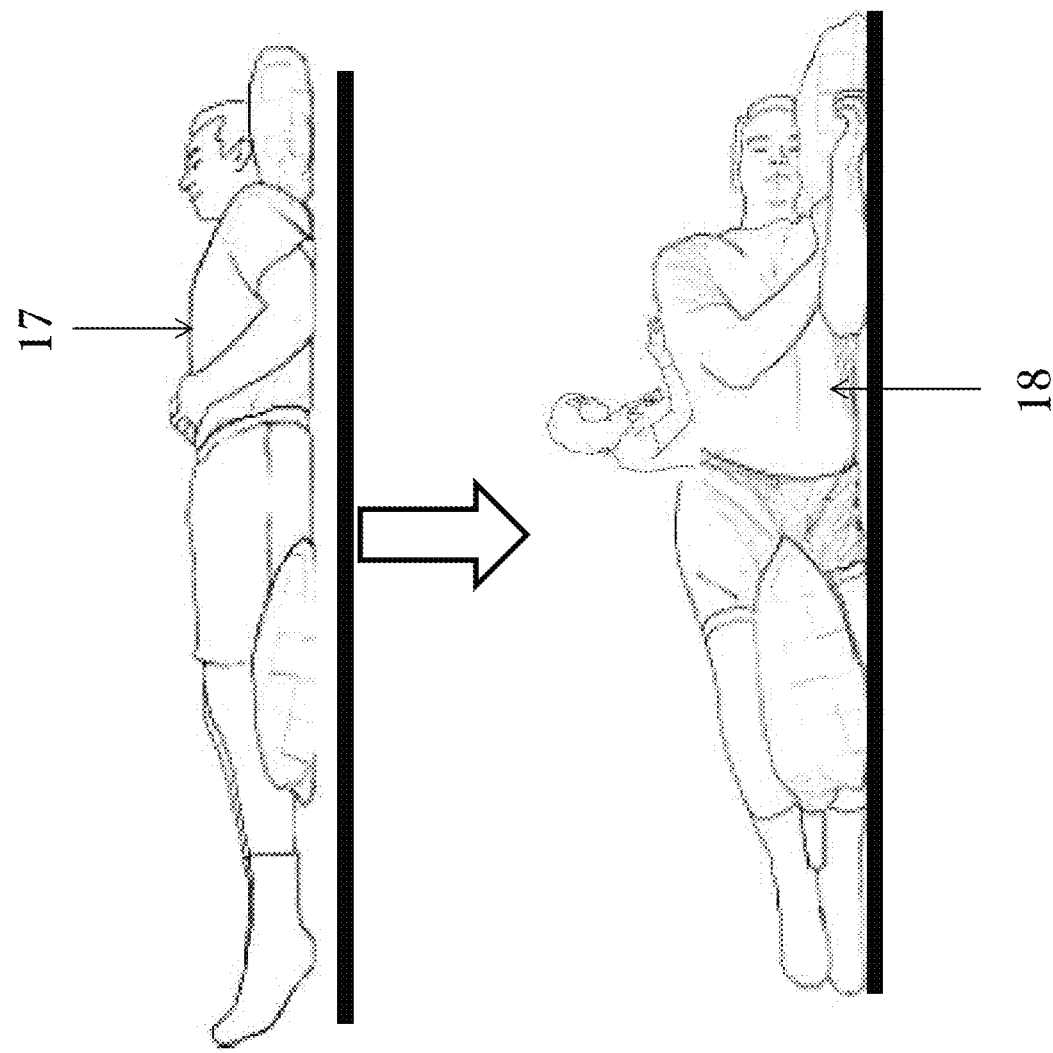

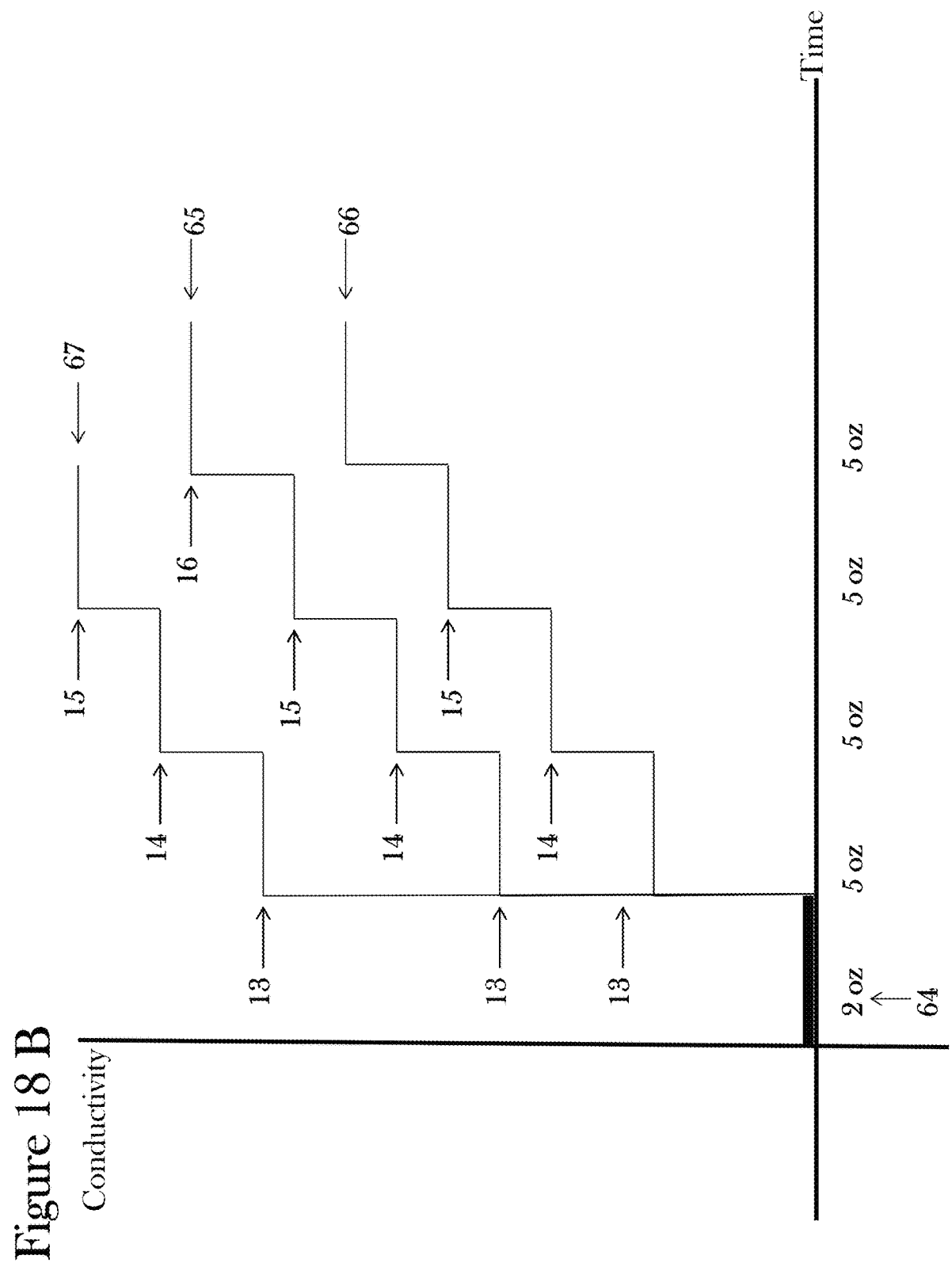

INCONTINENCE DETECTION SYSTEM

CROSS-REFERENCE TO RELATED APPLICATIONS

This application claims priority to U.S. provisional patent application No. 62/827,678, entitled "WE SENSE: SMART BRIEF, GREAT RELIEF," filed on Apr. 1, 2019, and U.S. provisional patent application No. 62/931,488, entitled "INCONTINENCE DETECTION SYSTEM," filed on Nov. 6, 2019. The content of both application is hereby incorporated by reference in its entirety for all purposes.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION

Field of the Invention

The present disclosure relates to systems and methods for incontinence detection, in particular to systems and methods for detecting incontinence with a diaper attachment pod that is releasably coupled to the carbon lines provided in the diaper.

In another aspect, the present disclosure relates to systems and methods for saturation detection, in particular to systems and methods for saturation detection by taking into account the diaper wearer's orientation. Also, the present disclosure relates to orientation detecting and sensing device.

Description of Related Art

For many years, a variety of designs have been developed for detecting and signaling the presence of urine in a diaper. However, most of these designs require manufacturing modifications to ordinary diapers in order to be implemented. With manufacturing modifications, lot of changes and additional machineries are required to be implemented in the manufacturing process of the diaper.

For example, a pouch like insert is needed in the diaper to house an alerting device as disclosed in U.S. Pat. No. 8,884,769, or a multiple button seats are needed on the outside surface of a diaper to fasten the alerting device as discloses in U.S. application Ser. No. 13/064,832, or embedding the urine sensing electrodes in between different layers of the diaper padding as discloses in U.S. Pat. No. 9,291,589. In some other cases, for example U.S. Pat. No. 4,106,001 discloses a device for detecting unintentional urination with a pair of spaced electrodes being adhered to the surface of the undergarment and being directly connected to an alerting device that is clapped over the waistband of the diaper. Also, U.S. application Ser. No. 15/388,278 discloses a wetness sensing and alerting system in which an alerting device is wrapped around by a sensor strip.

Further, the wetness sensor and the alerting device are configured as non-detachable in some prior art systems, wherein the entire device must be discarded when the wetness sensor becomes worn. Thus, such alerting devices become relatively expensive to manufacture. U.S. Pat. No. 5,838,240 discloses a wetness sensing and alerting system that are detachable from each other with the alerting device being adhesively bond to the outside surface of a diaper. While this system is useful as a wetness sensing and alerting system, it is dissimilar to the invention described herein, and lacks certain features and functional benefits, such as a need to clean up any left behind adhesive residue prior next use, which would be apparent to those skilled in the art by reading the detailed description accompanying with the drawings and the claims below.

Other designs use conductive leads as sensors to detect changes in electrical property of a diaper due to urination. Such sensors can also be placed over an inner layer of a diaper such that the sensors face user of the diaper. Even though lot of care is taken to make such sensors from materials that do not cause irritation to the user, the satisfaction of the user remains doubtful. Another way of detecting moisture inside a diaper is to use temperature sensors. In U.S. application Ser. No. 11/589,414, a temperature sensor is fastened to an interior surface of a diaper. A window or a cut out or a pocket on the diaper is present to make the temperature sensor visible from outside. However, the window is provided with a thermal insulating feature to avoid ambient temperature to affect the temperature sensor. However, such kind method to detect presence of moisture in a diaper using temperature sensor would require modifications in manufacturing process of an ordinary diaper.

Furthermore, in the prior art, there is no disclosure that takes into account the orientation of a diaper's wear when determining the saturation of the diaper. And no disclosure in the prior art suggests or teaches determining the amount of wetness by creating a baseline point.

BRIEF SUMMARY OF THE INVENTION

Many care facilities have no efficient way to determine, monitor, and schedule service and visits based on the real time needs of the patient. Patients are often left in their own urine and feces for extended periods of time, which may cause health problems. This leads to an increased demand for alternative incontinence management solutions. In accordance with the present subject matter, we have invented a sensor system for monitoring adult incontinence in patients/residents and for facilitating timely attention to resident needs in an institutional setting. This system not only facilitates things for the residents, but also for their caregivers too.

In the preferred embodiment of the current invention, there are two carbon lines along the length of an impermeable layer of an incontinence product (such as but not limited to diapers, briefs, under pads, fitted briefs, belted shields, liners, all-in-one pads, pull-up incontinence pants, protective underwear). For the purpose of clarity, in this application, a diaper will be used to illustrate the possible embodiments of the invention. In the healthcare context, a diaper is an absorbent pad made of one or more various materials and used for personal hygiene.

Our invention uses a sensing system that sends an alert via wireless transmission to the caregivers informing them that it is time to change a resident's brief. The invention includes a pod which is comprised of a printed circuit board, that, when placed upon the font of the brief, lines up with the sensor lines through capacitive coupling. It provides a means to measure the level of the diaper saturation with regards to the positioning of the resident. In this system, there is also a gravity sensor which can detect the orientation of the resident. For example, if the resident has a wetness event in different positions such as sitting, lying, or lying on the side, the system will automatically adjust the threshold level of diaper saturation, and, therefore timely send the brief changing alerts to the caregivers when a change is needed. The invention helps to avoid leakage and health problems such as skin irritations.

BRIEF DESCRIPTION OF THE DRAWINGS

FIG. 2A demonstrates the top view of two carbon lines printed on a plastic film in the preferred embodiment and how the Pod is connected to the sensor.

FIG. 4A illustrates the graph of conductivity vs. time for the sitting position.

FIG. 5A illustrates the graph of conductivity vs. time for the lying position.

FIG. 5B demonstrates the left side-view of what is occurring with each wetness event in the lying posture.

FIG. 5C depicts the top view of the diaper as it becomes saturated in the lying posture.

FIG. 6A illustrates the graph of conductivity vs. time for the sideways position.

FIG. 6 B.5 illustrates a comparison between conductivity vs. time for the urination events in different postures.

FIG. 7A illustrates a patient who has not moved within 2 hours and is rolled over by the caregiver.

FIG. 18 B illustrates a comparison between conductivity vs. time for the urination events in different postures with the creation of a baseline in another embodiment.

DETAILED DESCRIPTION OF THE INVENTION

Figure 1A:
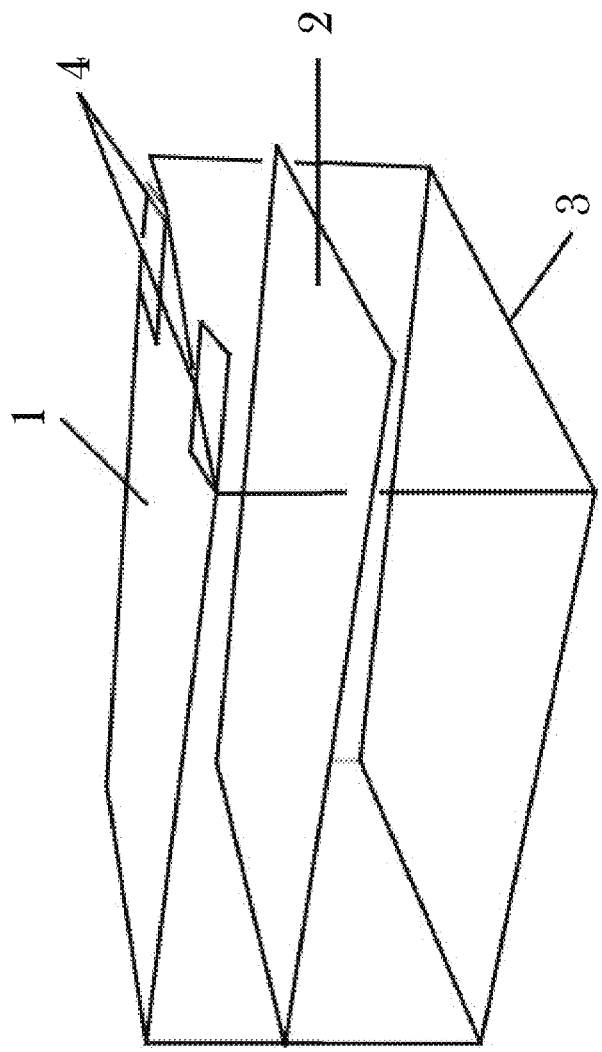
FIG. 1A illustrates a section view of the general structure of a standard diaper.

FIG. 1A illustrates the general construction of a diaper. A diaper is a product that allows the wearer to urinate or defecate without the use of a toilet. The most important characteristic of a diaper is its ability to absorb and retain moisture; it absorbs and holds waste products to prevent contamination of the clothing or external environment. When diapers become saturated, they require changing by a person such as a caregiver or nurse. Besides diapers, there are numerous other types of incontinence products such as under pads, fitted briefs, belted shields, liners, all-in-one pads, pull-up incontinence pants, protective underwear, and incontinence guards that can be used in our invention. It is to be understood that the list of incontinence products identified above is not an exhaustive list and that other absorbent articles and garments are within the scope of the present invention. It is also to be understood that a reference in this specification to any one such article, such as a "diaper" is to be taken to be a reference to any and all other suitable absorbent articles including incontinence garments, pads and the like.

Disposable diapers and incontinence products consist of a layered construction. This allows the urine to be distributed and transferred to an absorbent core structure where it is locked in. The core layer 2 which consists of the absorbent part is made up of hydrophilic superabsorbent polymers (SAP) and fibrous material. The polymers act like tiny sponges that retain many times their weight in water. These molecules can be distinguished as long chains and can be cross linked to form a gel network that is insoluble, but can absorb large amounts of water. This superabsorbent core can be thought of as a sandwich, connected between two sheets of nonwoven fabric: a permeable top sheet 1 and an impermeable bottom sheet 3. Nonwoven fabric is a fabric-like material made from long fibers which, in turn, form the body of the diaper. They are flat sheets made directly from separate fibers or from plastic film such as nylon, polyester, polyethylene, or polypropylene. They provide not only absorbency power, but they also supply cushioning, stretch, and comfort. The absorbent pad 2, the top sheet 1, and the bottom sheet 3 are three separate components in long rolls, which are joined together in the diaper making machine and finally cut into individual diapers. The assembled diaper may have other attachments, such as Velcro or tape 4 which acts as closures.

Figure 1B:
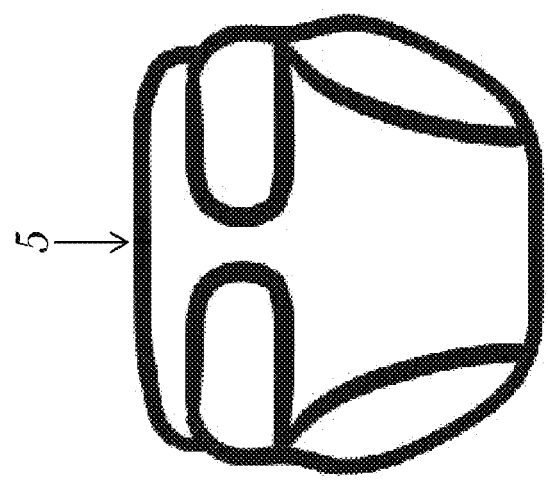
FIG. 1B portrays the actual look of a diaper once ready.

FIG. 1B shows the end result of the product. The layers of a diaper coming in long rolls are joined together in a specific fashion. First, the absorbent core layer 2 is vacuum-formed, then connected to the top 1 and bottom 3 nonwoven fabric sheets. This is accomplished by feeding the absorbent pad onto a conveyor with the polyethylene bottom sheet. The polypropylene top sheet is then fed into place, and the compiled sheets are joined by gluing, heating, or ultrasonic welding. Finally, elastic fibers are attached to the sheets to hold the edges of the diaper and allow it to retain its shape. The long rolls are then cut into individual diapers 5, folded, and packaged for shipping. The diaper 5 is properly fitted on a resident; it will allow the bodily fluid to pass through the permeable top sheet and be absorbed into it.

Referring to FIG. 2A, in the principal embodiment of our current invention, there are two carbon lines 6 along the length of the diaper printed on a plastic film or an impermeable layer. These 6 are basically the sensor strips which consist of inkjet-printed or any other method of printed carbon lines, including but not limited to rotogravure, flexo-gravure, screen printing, and offset printing etc. These carbon lines 6 are printed on the impermeable layer in the preferred embodiment before the separate diaper sheets (explained in FIG. 1B) are glued together to make the final brief product. In other embodiments, the sensor strips can be printed on any other layer and can be made of silver or any other material that has electrical conductivity. They 6 are designed to function properly regardless of the humidity of the diaper and also do not affect the absorbency of the diaper padding. In the preferred embodiment of the present invention, these lines 6 have a resistance of approximately 100 kΩ/diaper. If the length 7 of a diaper is, for example, 30 inches, which is a standard sized diaper, then, we will have about 3 kΩ/inch of resistance. In the primary embodiment, there is also a Pod 8, which is an alerting device. The purpose of such a device is to transmit individual wetness alerts to the caregiver via Wi-Fi to an App using a unique sensing system. In our invention, the Pod 8 clips on the front of the brief 5. In this Pod construction 8, there is an electric circuit which compromises of a battery, a Wi-Fi chip, and other electronic components. The contact terminals on the Pod 8 and the sensor strip 6 should be properly aligned with each other. Although the Pod 8 cannot make physical contact with the sensor 6 due to the nonwoven layers 1, 3 which are present on each side of the diaper, it 8 is close enough to those carbon resistive lines 6 in order to make capacitive contact. In our current invention, this electrical connection is temporary, such that the alerting device 8 can be released from the brief 5 when a diaper change is needed, and the alerting device 8 is then ready for immediate use. The Pod 8 can quickly be attached to the new brief 5 by clipping it 8b to the front of it 5. You can pinch the Pod 8 with your hands to open and close it. The Pod 8 sends across 3.3 V pulses in the preferred embodiment. When the diaper 5 is dry (not saturated), the electrical circuit is open and there is no current passing through. On the contrary, if there is a presence of urine 9, then, there is a contact. Now, let us explain how this contact is established. Since urine 9 contains sodium chloride ions among other ions, it acts like a conductor and will form a closed electrical circuit, allowing current to flow and creating a means for the signal to travel back. As the volume of the urine 9 gets bigger and bigger, we see less and less resistance because the distance between the Pod 8, the urine line, and the whole path of conductivity 9 becomes shorter. The conductivity of the urine 9 is very high compared to the conductivity of the lines 6, and the resistance of the lines 6 is very high compared to the resistance of the urine 9. There is a direct relationship between the resistance, and the length between the Pod 8 and the urine 9. The greater the distance, the higher the resistance will be, and the shorter the distance, the lower the resistance will be. The pulse travels through the urine 9 and comes back as current, measured in amperes. This allows us to measure the resistance 10 in each direction. If the pulse that we get back is small, then, the resistance will be high. Therefore, the smaller the pulse, the higher the resistance will be. As the resistance decreases, the value of the pulse increases. Hence, there is an inverse relationship between the current and the resistance, as, (R↑ causes I↓).

Figure 2B:
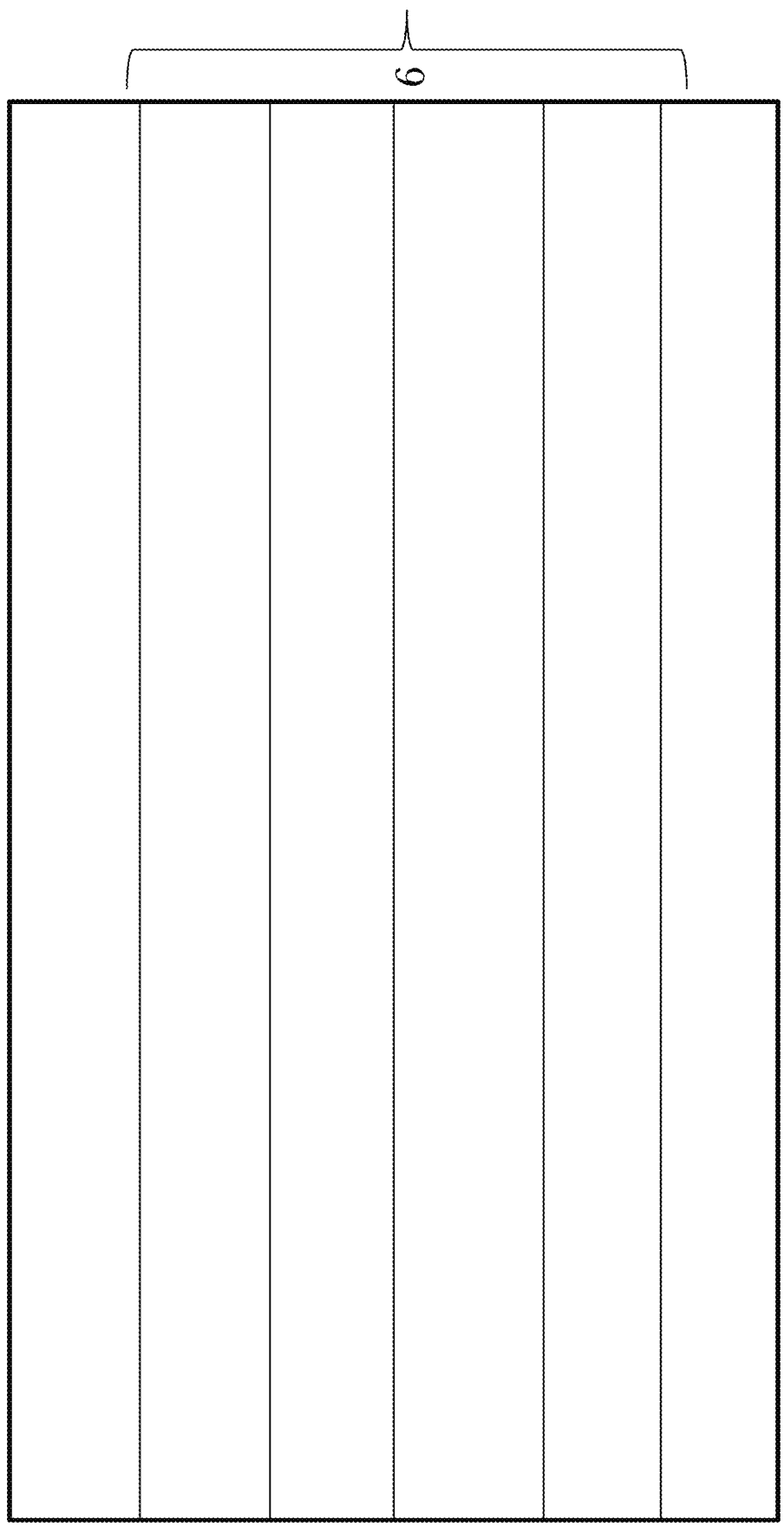
FIG. 2B illustrates a top view of multiple carbon lines printed on the plastic film in another embodiment.

FIG. 2B illustrates the fact that in other embodiments, the carbon resistive lines 6 can consist of multiple lines, three, four, and, so on. The length and width of the carbon bands 6 are adjusted according to the variation in diaper size.

Figure 3:
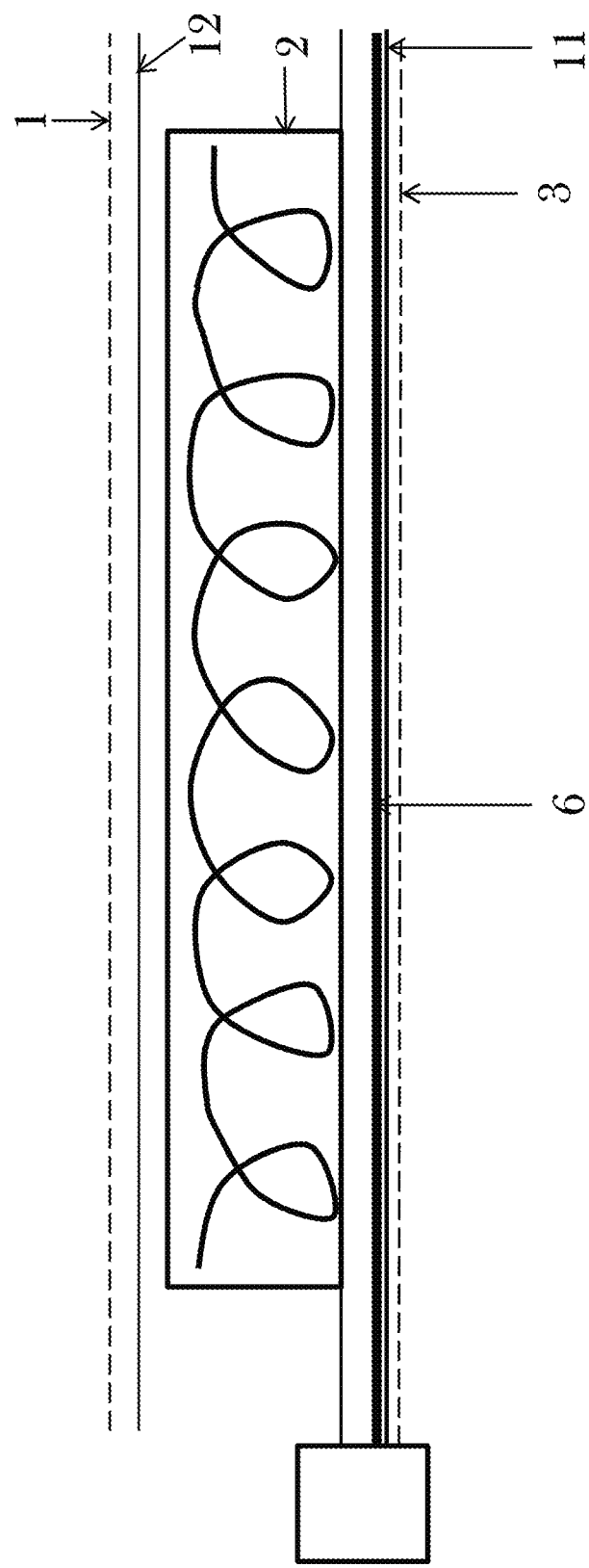
FIG. 3 depicts the cross-sectional view of the structure of a standard diaper imbedded with We Sense technology.

FIG. 3 demonstrates that in our invention, the carbon ink lines 6 are printed on a plastic film or an impermeable layer 11 in the preferred embodiment. Underneath the core 2 (absorbent pad layer), there is the impermeable layer 11 containing the printed carbon ink lines 6, which are the sensors. Underneath that, there is the nonwoven layer 3. On top of the absorbent pad 2, there can be extra layers such as a hydrophobic layer 12. At the very top, there consists of another nonwoven sheet 1. In other embodiments, there can be extra layers above and under the core 2 to provide extra support and comfort. All these materials are available in big rolls, and are injected into a diaper making machine that glues the sheets together, and, finally, the diaper 5 is made.

Referring to FIG. 4A now, the graph represents conductivity vs. time. Each step on the graph depicts a time when the resident urinates. It is essential to determine a threshold of diaper saturation, for instance, to avoid skin irritation and unnecessary accidents. This will provide the highest level of care to residents and also allow the caregivers to save time and energy. A threshold of diaper saturation simply means that the diaper is wet enough to require changing. In this example, in the preferred embodiment, a resident urinates 5 ounces every 15 minutes while sitting. It can be seen that the first time the resident urinates 13, there is no need for a diaper change since the appropriate saturation level required for it has not been achieved. Conductivity increases with respect to each wetness event. He micturates again a second time 14, and, then, a third time 15, and there is a rise in conductivity, respectively. However, at this time, there is still no need for a diaper change because the diaper is not saturated enough. Next, upon the fourth wetness event 16, we realize this point 16 is "the threshold of diaper saturation" in the principal embodiment because the diaper needs to be changed now. We made that decision based on test results and accurate findings. In this example, the diaper is saturated at point 16 meaning the resident has urinated 20 ounces. It is wet enough at this point 16 such that this happens only when the resident is sitting down in the preferred embodiment. Moreover, in our example, since the diaper 5 reaches a saturation level of >70% at this point 16 in the preferred embodiment, an alert is sent to the caregiver that it's time to change the residents' brief.

Figure 4B:
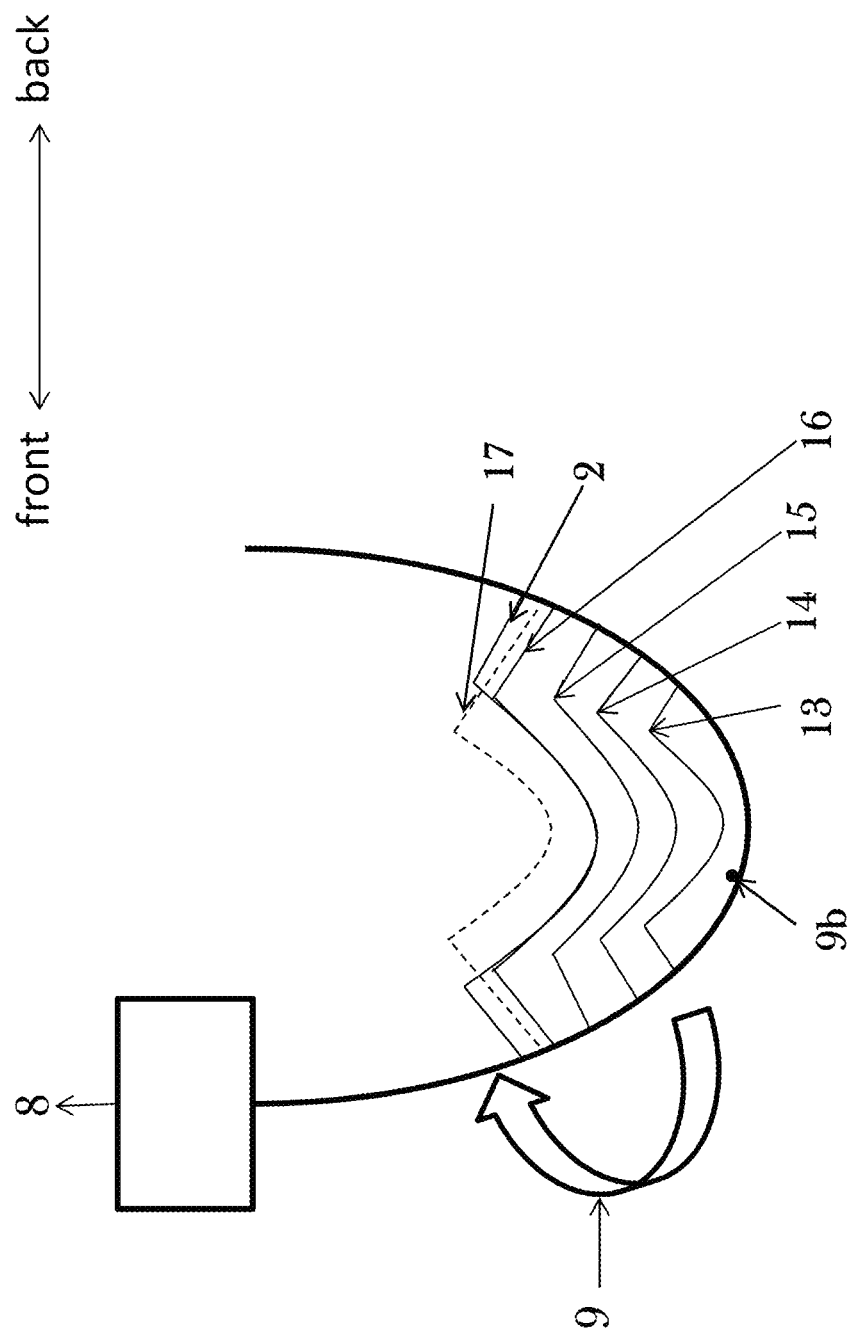
FIG. 4B demonstrates a side-view of what is occurring with each wetness event in the sitting posture.

Looking at FIG. 4B, we analyze what happens inside the pad when the resident micturates in the sitting posture. In this example, the first time the resident urinates 5 ounces, and the urine injection point is at 9b, and it fills up this 13 much of the diaper. The second time upon urination, another 5 ounces 14 is filled up, but it is still not saturated enough for the system to say it's time to change the brief. The urine 9 travels up the diaper 5 due to the fibers, and the absorbent core of the diaper is represented by number 2. The numbers represented in the drawings are only for illustration purposes. More fluid accumulates a third time 15, and upon the fourth time 16, the resident has urinated 20 ounces. In this example, we can see the diaper 5 is now saturated enough at point 16 for the brief changing alert to be sent in the primary embodiment. Results from experimentation revealed that this point 16 is now more wet and requires changing. If the resident urinates for a fifth time 17, it can be clearly seen from the diagram that the brief 5 will leak, because the absorbent core 2 of the diaper is full. In other embodiments, the location of the saturation point for the brief changing alert to be sent can vary depending on the sitting angle, for example. The Pod 8 has an orientation meter with respect to gravity. One can tell the orientation of it, and, based on that, one can adjust where he thinks it is required for the resident to be saturated. In addition, there is a greater propensity for the urine 9 to travel up in this posture when compared to the laying position.

Figure 4C:
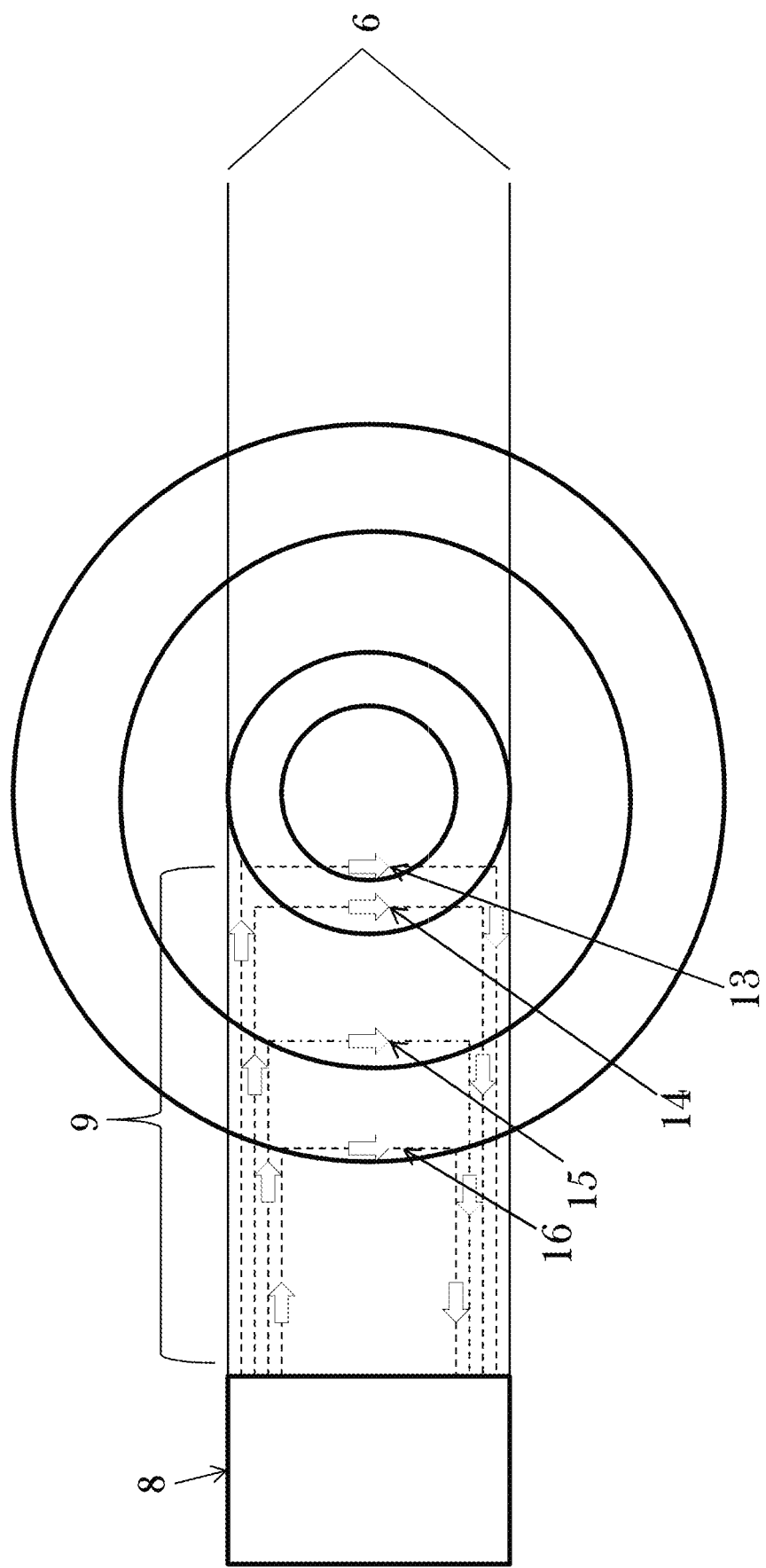
FIG. 4C depicts the top view of the diaper as it becomes saturated in the sitting posture.

In FIG. 4C, a cross-sectional view of what is happening can be seen. In regards to the first wetness event 13, it can be noticed that at this point there is the highest resistance and lowest conductivity. By highest resistance, it is meant that the distance is greatest between the Pod 8 and the first urine line of contact 13. By the time the second event takes place, it can be seen that the saturation point is now here 14. A decrease in distance has occurred when compared to the former point of contact 13. The resistance is lower than the previous point 13, but the brief 5 is not saturated enough for change. With the third occurring event 15, the pool of fluid increases and the point of saturation moves closer to the Pod 8, and a greater decrease in resistance takes place as the distance gets shorter than the previous two points 13, 14. Conductivity starts to increase as resistance begins to decrease. However, the brief 5 is still not wet enough to require changing. Finally, upon the fourth wetness event 16, the distance has decreased a lot and so has the resistance, but conductivity has risen. Hence, in the preferred embodiment of our present invention, this point is declared as the "threshold of diaper saturation" in the sitting position. This means that in this example, the alert to the caregiver is sent earlier. The alert notifies the caregiver of how much saturation there is and when it is time to change the resident's brief. This illustration vividly depicts that the resistance varies directly with the distance between the urine line of contact 9 and the Pod 8. Fluid 9 can travel more easily up in the sitting position; hence, saturation occurs at a higher pace than in the laying position.

In the preferred embodiment, as shown in FIG. 5A, each step in the graph demonstrates that the resident urinates 5 ounces every 15 minutes, but now the orientation of the resident has changed from sitting to lying down. In this example, the first time the resident has a wetness event 13 while in the lying down or flat posture, conductivity rises. At this time, there is no need to change the diaper since the appropriate saturation level required for the brief change has not yet been achieved. Upon the second occurrence 14, conductivity rises higher, but it is still not time to change the brief yet. Then, upon the third event, a rise in conductivity is perceived again, and this point 15 is marked as the "threshold of diaper saturation" in the preferred embodiment. The brief has reached a saturation level of >70%, and a brief changing alert should be sent to the caregiver at this time in the principal embodiment. Based on our experimentations and test results, in the preferred embodiment, the threshold of saturation here in the flat position is set at a lower point 15 instead of, for example, at point 16 like in the former sitting posture. In conclusion, it is proven that when the resident is lying down in the principal embodiment, saturation occurs at an earlier rate when compared to the saturation point of sitting.

Referring to FIG. 5B, an analysis is shown concerning which parts of the diaper 5 become saturated with each wetness event in the lying down or flat position. In this example, in the preferred embodiment, for the first wetness event, the urine spot is at 9b, and it fills up this much of the diaper 5 with 5 ounces 13. When the resident micturates in this position, the concentration of the urine 9 will become larger and larger, and most of it 9 will pool in the back. The second wetness event accumulates 10 ounces of liquid 14, but it is still not saturated enough for the system to say it's time to change the brief 5. More fluid 9 accumulates a third time (15 ounces of urine) and we notice that this point 15 is "the threshold of diaper saturation" in our example in the preferred embodiment. If the resident were to urinate again for a fourth time 16 like in the sitting example, it can be observed from the diagram that the brief 5 will leak because the absorbent core 2 of the diaper is full. In other embodiments, the location of the saturation point for the brief changing alert to be sent can vary. In contrast to the previous example, in FIG. 4B, the threshold is attained at a later point 16. The Pod 8 has an orientation meter, and, therefore, knows the orientation of the resident. For example, on our phones, there is a gravity sensor, which can detect the phone's orientation when one tilts it or changes its position. Similarly, when the resident changes his position, the position of the Pod 8 also gets modified, and, hence, the Pod 8 can detect the orientation with respect to gravity. In this position, saturation has to have a higher resistance before the Pod 8 can send the alert stating that this diaper 5 is saturated enough. When lying down, most of the fluid 9 will not travel as far up quickly as it will when the resident is sitting down. In comparison, the alert to the caregiver will not be sent as early as it would be in the sitting position. Therefore, proper adjustments need to be made in the system that decides the different thresholds for when saturation is achieved in order to alert the caregiver much earlier and avoid leakage. There is a lower positioning point when the resident is lying down which means a higher resistance point, and a lower resistance point when he/she is sitting up, and variable in between when he/she is lying on the side, for instance. In summary, the threshold of saturation will depend on what angle the Pod 8 is at, and, separately, on the orientation of the resident (sideways, flat, sitting).

In FIG. 5C, in the preferred embodiment, the cross-sectional view of what is happening when the resident micturates in the lying position is shown. The pool of fluid gets bigger and bigger. In this example, it can be seen that at point 13, the resistance is very high upon 5 ounces of urination. At the second point 14, the resistance decreases somewhat, and conductivity begins to increase. Finally, this diagram clearly depicts that upon the third wetness event, the "threshold of diaper saturation" is at point 15 in the primary embodiment. Formed on accurate studies and test results, we see that in this example, the saturation point 15 is reached upon the 15 ounce of liquid mark. An alert is sent to the caregiver at this time to change the resident's brief. In comparison with the sitting posture, the saturation level is at point 15 instead of point 16. There is a lower resistance at this saturation point 15, and the system needs to send an alert much earlier, because there is a greater chance of leakage. Hence, the resistance required to say whether or not the diaper is saturated is increased. That is because there is a lesser propensity for the urine 9 to travel up in the sideways and lying posture. Therefore, it 9 is pooling in the back, and there is a higher level of alert already. By taking all of this into account, proper adjustments need to be made in order for the caregiver to receive the alert at the appropriate times to prevent any accidents, reduce the workload, and create positive change.

Referring to FIG. 6A, the conductivity-time graph illustrates a resident who has wetness events in a third position, lying on the side. Similar to the sitting and lying position, an increase in conductivity can be seen with each wetness event. In the primary embodiment, in this example, the resident's first wetness occurrence 13 indicates 5 ounces of urine. By the time, the second event happens, 10 ounces of liquid has filled the diaper, and we identify this point 14 as "the threshold of saturation" in this example in the preferred embodiment. The brief has now reached a saturation level of >70% in the principal embodiment. It can be observed that with each angle, the threshold varies more and more. In other embodiments, we change the location where we say it is saturated or not to send the brief changing alert. For example, the sideways is the in-between position compared to the sitting and lying positions, and it is an extrapolation. This means that there are many different points to determine whether the brief should be saturated or not. For instance, if the level of degree in the sideways position is 10° or 20°, or 45°, then, the point of saturation will vary more and more with each angle. We are able to conclude that, from our examples, in the sitting position, the threshold level was achieved at 20 ounces of liquid mark; hence, there was a higher saturation point when compared to the lying and sideways positions. In comparison with the sitting posture, there was a lower saturation point in the lying position; it was achieved at 15 ounces of liquid mark, and in the sideways posture, we decided to mark the threshold at an even lower saturation point at 10 ounces. Again, we reached this conclusion built on proper research and examinations.

Figure 6B:
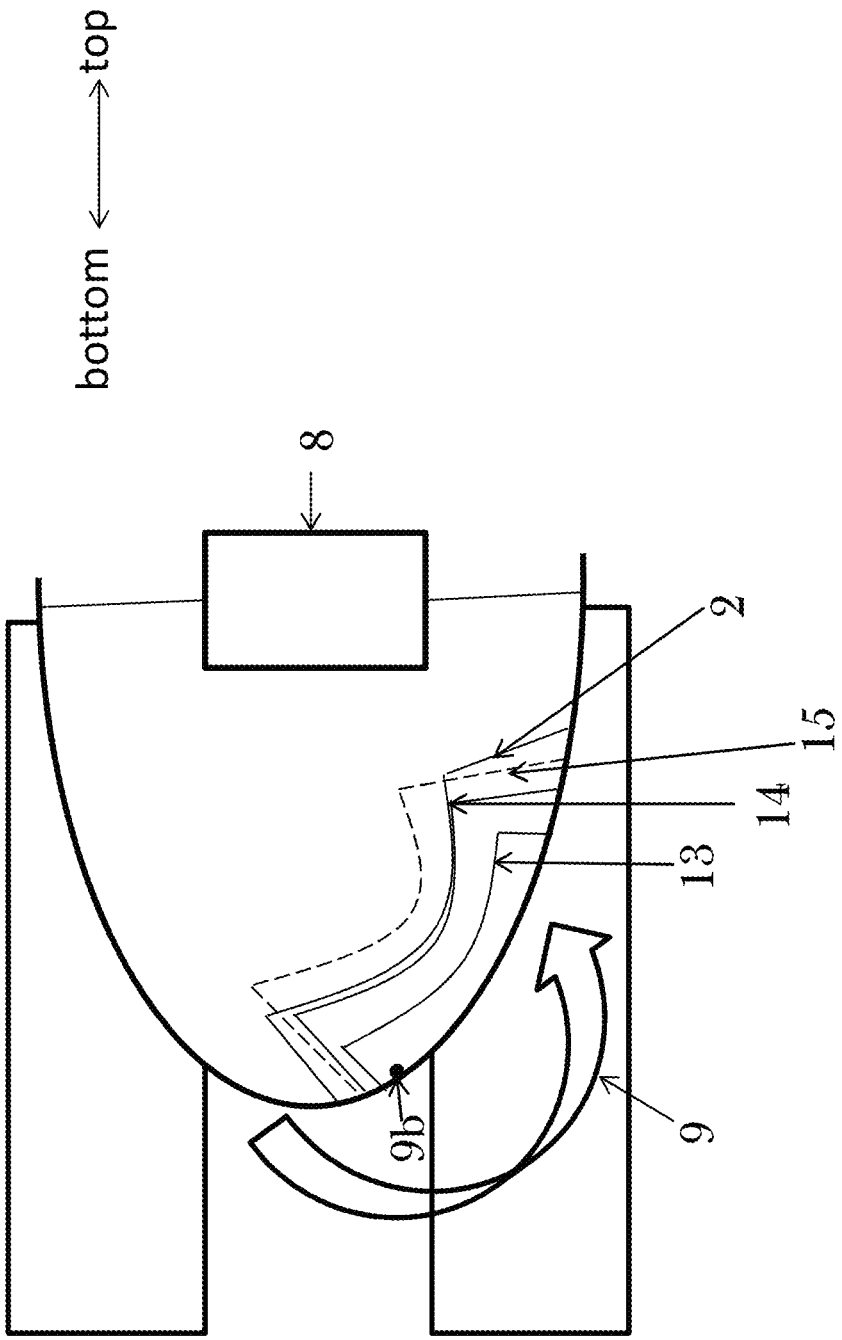
FIG. 6B demonstrates the front view of what is occurring with each wetness event in the lying on the side posture.

Referring to FIG. 6B, the wetness points when the resident is in the sideways position will be analyzed. Here, the urine spot 9b will not be in the center. The first wetness event indicating the 5 ounces mark saturates the diaper 5 at position 13. The second time indicates the 10 ounces mark as the liquid reaches this point 14. In this example, in the preferred embodiment, it can be vividly seen that saturation occurs at this point 14 because this happens only when the resident is lying on the side. It can be proven from experimentation that this is now more wet; hence, in this position, an alert to the caregiver is sent much earlier because there is a greater chance of leakage. It is highly undesirable for the fluid 9 to leak, because that would mean extra laundry, and extra costs/work load. Again, in comparison with the threshold of saturation in the sitting position 16, the threshold level of saturation here 14 is attained earlier. Therefore, one can increase/decrease the resistance required to say if the diaper is saturated or not, so all the alerts get reduced/increased depending on the residents' side angle, and on the angle of sitting and lying down.

Referring to FIG. 6 B.5, the graph represents a comparison of conductivity vs. time with regards to the resident's urination events in each of the three different postures: sitting 65, lying down 66, and lying sideways 67. Each step on the graph depicts a time when the resident urinates. It is essential to determine a threshold of diaper saturation, that is when the diaper is wet enough to require changing. In this example, in the preferred embodiment, a resident urinates 5 ounces every 15 minutes in each of the three varying positions. It can be seen that the first time the resident urinates 13, conductivity is lowest in the lying down position 66, highest in the sideways position 67, and in-between in the normal, sitting posture 65. This pattern continues with each urination event, and one can see a rise in conductivity. In the sitting position 65, upon the fourth wetness event 16, we realize this point 16 is "the threshold of diaper saturation" because the diaper needs to be changed now in the principal embodiment. In contrast to this, "the threshold of diaper saturation" is reached earlier in the lying down 66 and lying sideways 67 positions at point 15. We made that decision based on test results and accurate findings.

Figure 6C:
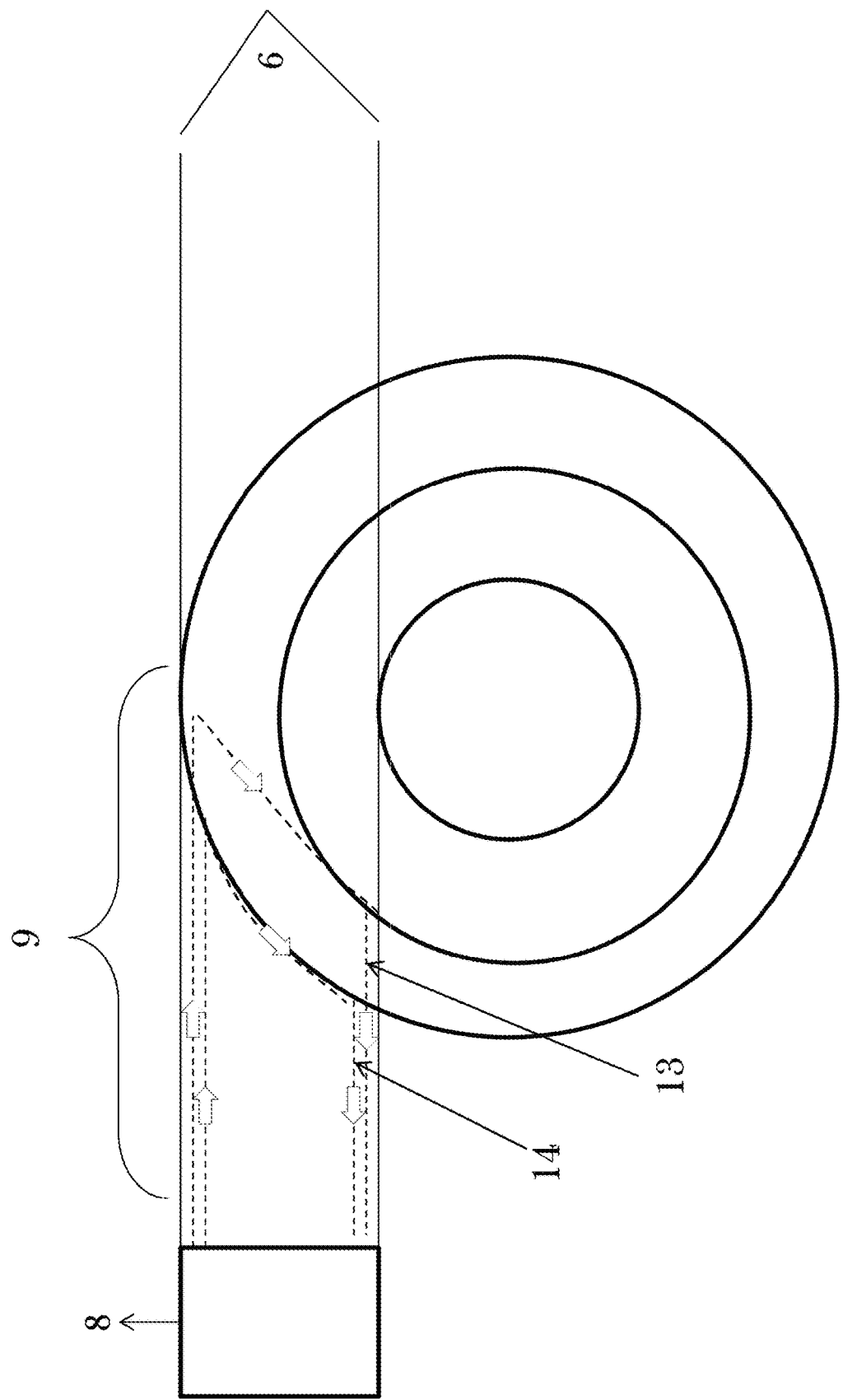
FIG. 6C depicts the top view of the diaper as it becomes saturated in the sideways position.

Referring to FIG. 6C, a cross sectional view of the diaper is illustrated. The diagram clearly depicts that for the first wetness event (5 ounces mark), the point of contact is not in the center in the sideways position. Resistance is very high at this point 13, and conductivity is very low. Resistance is inversely related to conductivity. The second wetness event (10 ounces mark) demonstrates that the resistance has decreased from the previous point 13, and it was decided to mark the threshold saturation level at this point 14 in the preferred embodiment. When it reaches this point 14, the brief needs changing, and, again, we realize this based on reliable test results and findings. It can be clearly observed that this saturation point 14 is attained much earlier compared to the saturation threshold in the sitting posture 16 in the principal embodiment. In other embodiments, this threshold value will vary. For instance, the amount of urine, how an individual is oriented, and the orientation of the Pod 8 all play a role in order to effectively determine the "threshold level of diaper saturation."

Referring to FIG. 7A, a resident who is lying in the same position 17, and has not moved for two hours is shown. In nursing centers and hospitals, the majority of people have some kind of dementia; they are not mobile. If you lie for a long time, you can get pressure ulcers (also known as bed sores) and skin ulcers which can prove to be very dangerous. Pressure ulcers are injuries to the skin and underlying tissue resulting from prolonged pressure on the skin. In nursing centers, residents who are at risk of bedsores are those with a medical condition that limits their ability to move/change positions or those who spend most of their time in a bed or chair. Primary prevention is to redistribute pressure by regularly turning the person, and our present invention is made to sent an alert to the caregiver to do just that. In the preferred embodiment of our current invention, the resident should move every two hours; the Pod 8 that is fastened to the font of the brief 5, will sent a moving alert to the caregiver to roll over the resident if he has not moved by himself every two hours. If he has moved, then, the moving alert will be canceled. Since the caregivers do not know whether the resident has moved or not every two hours, our invention provides a complete solution to resolve this issue. The Pod 8 has a sensing system which it uses to detect the residents' orientation with respect to gravity. It can detect whether the resident has moved or not by a certain amount of degree. In this example, in the preferred embodiment, the resident is lying in the straight position 17, and he has not moved for two hours. The sensing mechanism of the Pod 8 detects this and, hence, sends the moving alert to an App via Wi-Fi to alert the caregiver. Consequently, the caregiver comes to roll/turn over the resident, and his posture has changed from lying straight to the side position 18.

Figure 7B:
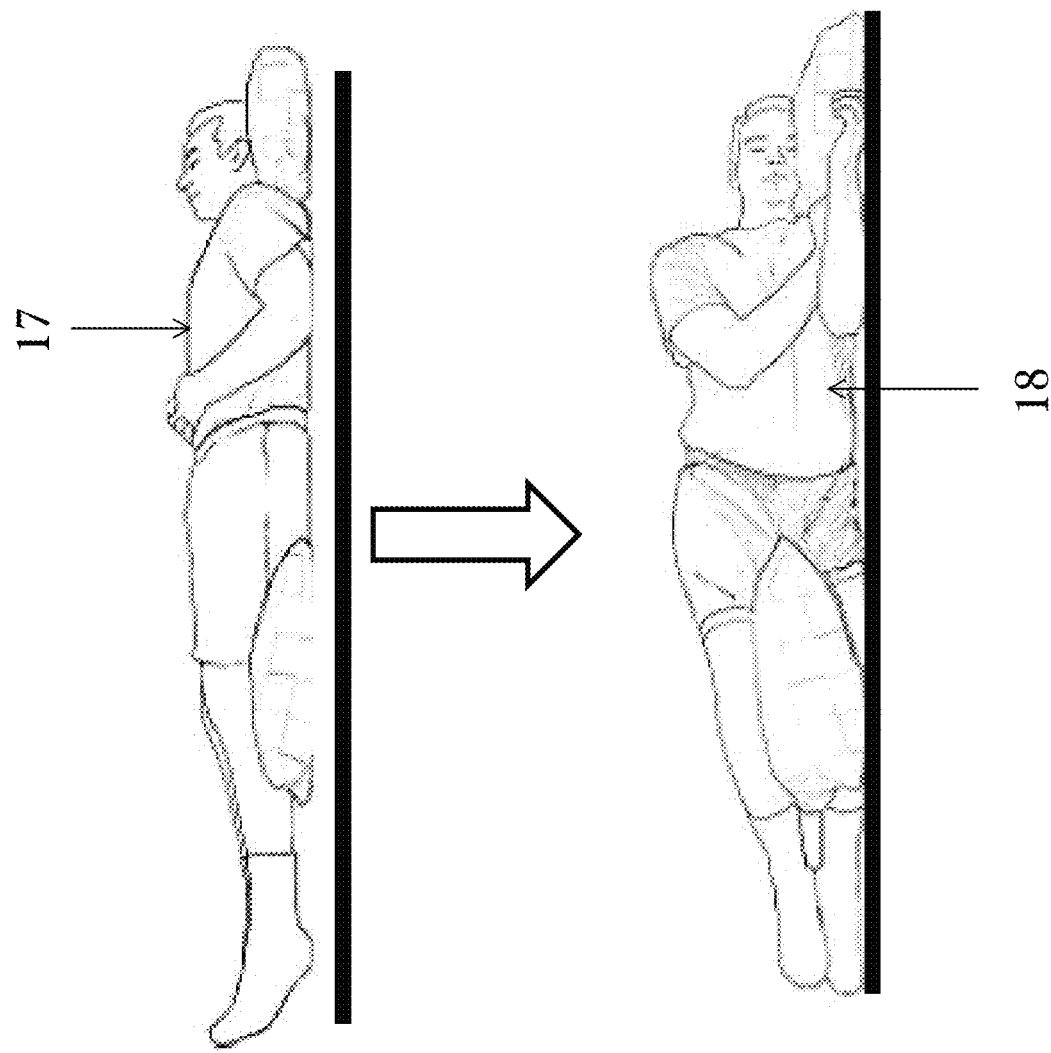
FIG. 7B shows a patient who has changed his position by himself within 2 hours in the preferred embodiment.

In FIG. 7B, it shows the resident is shown in the lying down position 17. The Pod 8 is continuously monitoring the orientation of the resident with respect to gravity. It can detect whether the resident has moved or not by a certain degree of angle. In this example, in the principal embodiment, the resident is lying in position 17. Within the two hour range, the Pod 8 senses that the resident has changed his orientation to a new position 18. Hence, the moving alert is cancelled in this example of the preferred embodiment. In other embodiments, the time frame that is required for a resident's movement may vary.

Figure 8:
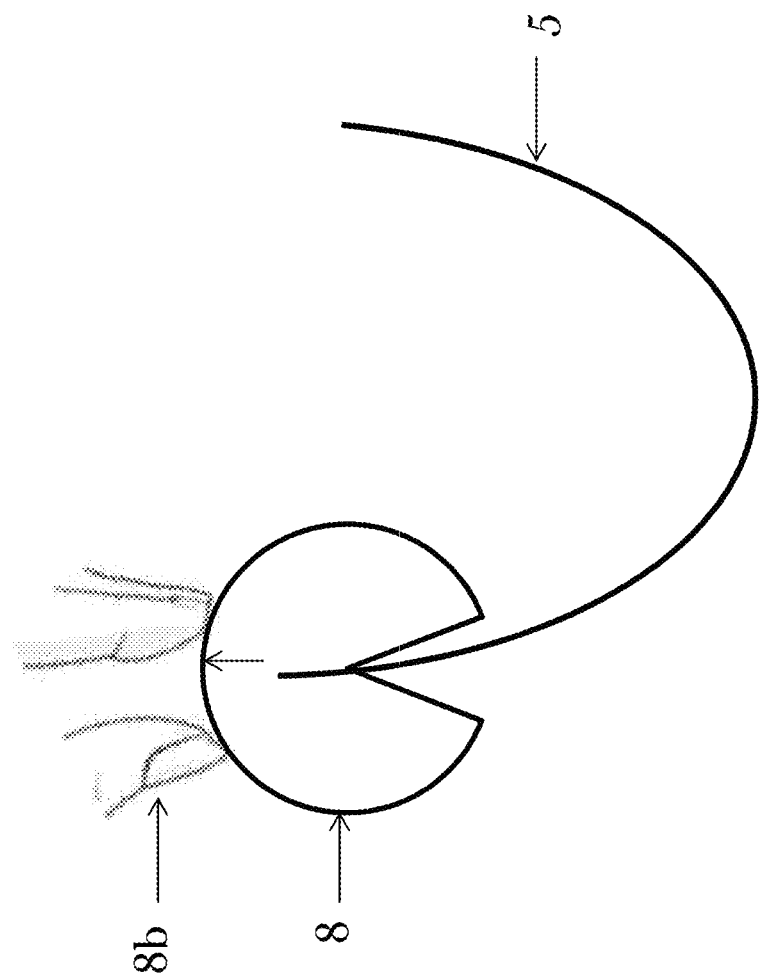
FIG. 8 shows a side-view of how the Pod opens and clips to the brief.

FIG. 8 illustrates how the Pod 8 clips on the front of the diaper 5. By pushing the top of the Pod 8 and putting some pressure with your fingers 8b, it 8 will open up, and you clip it 8 to the front of the brief 5. It 8 does not physically touch the sensor strips 6 which are printed on the impermeable layer of the brief 5 because there is nonwoven material covering the brief 5 on both sides.

Figure 9:
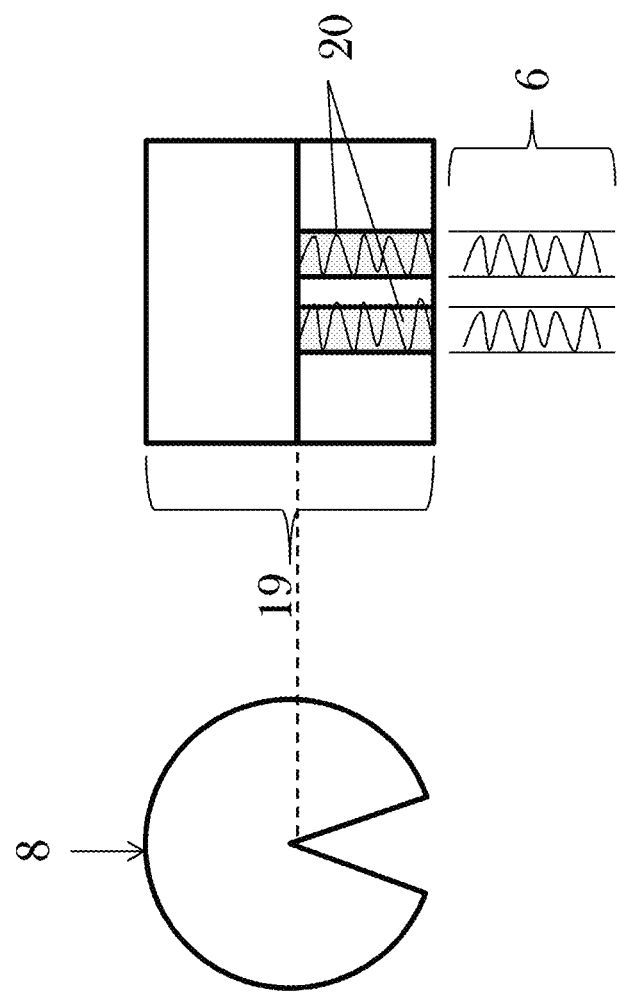
FIG. 9 is a cross-sectional view of the inner components of the Pod.

FIG. 9 demonstrates how the Pod 8 makes contact with the sensor lines 6 printed on the impermeable layer of the diaper 5. It was demonstrated in FIG. 8 that when one pushes the Pod 8, it opens up. A closer look will be taken as regards to how the Pod 8 works and what is inside the Pod 8. Inside the Pod 8, there is a printed circuit board 19, and there are also pads (a copper circuit) 20 on both sides of the Pod 8. In the preferred embodiment of our current invention, there are two pads 20, and they touch and line up with the sensor strips 6 on the brief 5. There are two carbon resistive sensor lines 6 in the preferred embodiment, and they 6 sandwich together with the pads 20, which are on both sides of the Pod 8. The pads 20 and the sensor strips 6 are not physically connected together. An explanation will be given in the following paragraphs as to how contact is established between the pads 20 even though there is no physical connection. In other embodiments, there can be more pads 20 as well as additional sensor lines 6.

Figure 10:
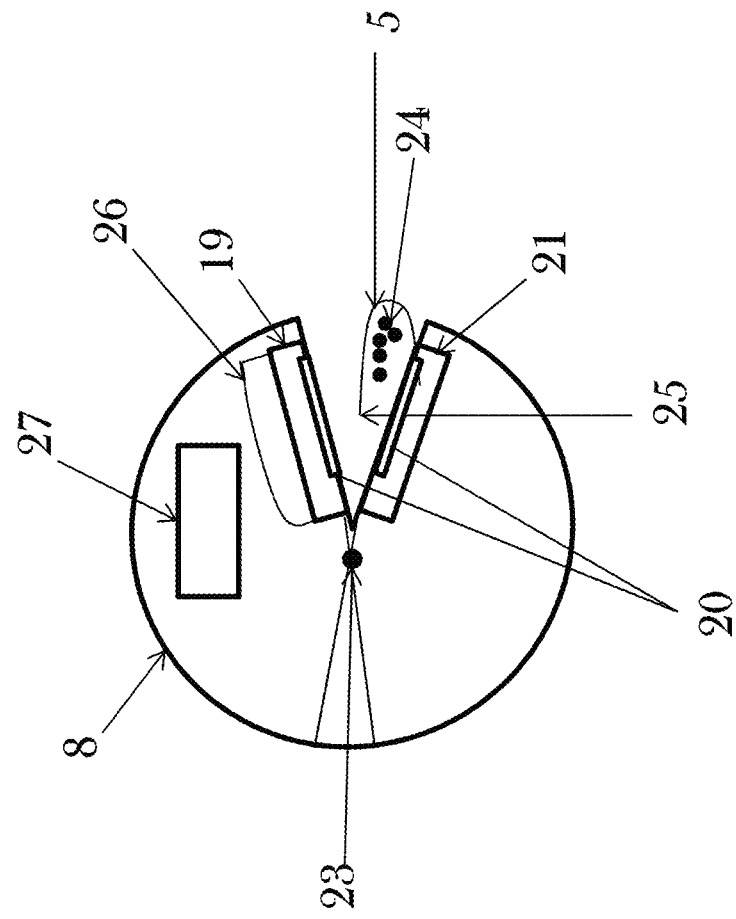
FIG. 10 illustrates the details of the inner components of the Pod

Referring to FIG. 10, a closer look at the inside construction of the Pod 8 takes place. On the inside, it is like a hinge 23. One can push the hinge 23 and the Pod 8 opens up. On one side, there is a printed circuit board (PCB) 19 and it has components 26. There are pads 20 on both sides in the preferred embodiment. In other embodiments, there can be additional pads 20. Now, let's talk about how do they make contact with each other. It is not possible to put wires here because it would be hard to assemble everything together. Instead of wires, a conductive foam 21 has been placed in the preferred embodiment. In other embodiments, it could also be foam with a conductive coating on top. Soft and compressible foam makes possible the electrical coupling of surfaces. The diaper 5 is only inserted up to a certain point. In the preferred embodiment, it is inserted only up to this point 25 because it was physically stopped 5 from going any further. Since it was stopped 5, there's a little bit of space left. Now, when the pads 20 close together, they 20 form a full circuit around. Pads are required on both sides because it increases the capacitive coupling between the two pads 20. A foam 21 is needed on one side or both sides, something squishy. For example, soft and compressible foam is needed to fill a gap while providing electrical contact. Conductive foams can be used to fill these spaces and electrically couple surfaces. Since the diaper 5 sometimes has some variations, for instance, usually some little SAP particles 24 could be stuck sometimes here at the top 25, and when you close the pads 20, there will be a gap. However, a gap is not desirable because it reduces capacitive coupling, and that's why there is the conductive foam 21 because the pads 20 should be as close as possible. The foam 21 is placed on the side of the Pod 8 where it is more likely to have these SAP particles 24. The foam 21 is also on the thinner side of the Pod 8, because this side goes on the belly of the patient, and, hence, it will not obstruct it. The printed circuit board (PCB) 19 and the battery 27 are on the other side of the Pod 8.

Figure 11:
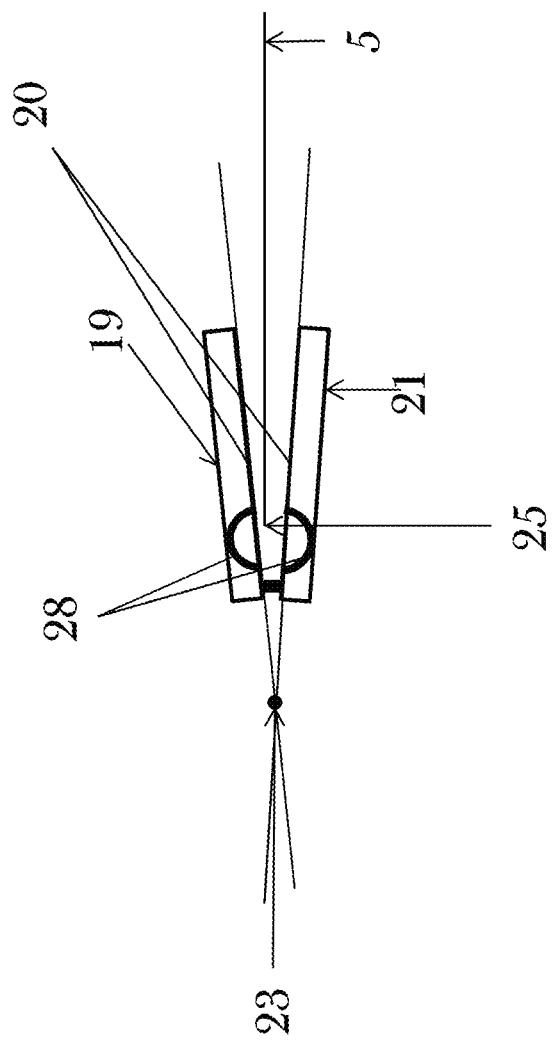
FIG. 11 depicts how the pads make capacitive contact inside the Pod.

FIG. 11 illustrates another example of how the pads 20 touch each other in another embodiment. When you close the Pod 8, the pads 20 are very close now; they are sandwiched together. There is the PCB 19, and there's the conductive foam 21; these two parts connect because they touch each other. In this location here, we have a hole or gap 28 in this example in another embodiment. We also have some insulation inside the Pod 8 because where the diaper 5 ends 25, it is cut, and there are little fibers that can be conductive. If they touch, then it causes errors in our reading; therefore, we do not want it to touch. Hence, a little gap 28 is necessary inside here, just in case somebody pushes the diaper 5 in too far. For example, if the diaper 5 gets shoved in too far, then, it will cause a bigger gap and will not allow the Pod 8 to close properly. In such a situation, if there is a hole like a bump 28, then, it will allow the Pod 8 to close properly and create a good coupling contact. The pads 20 will capacitively couple together with the sensor lines 6 on the diaper 5.

Figure 12:
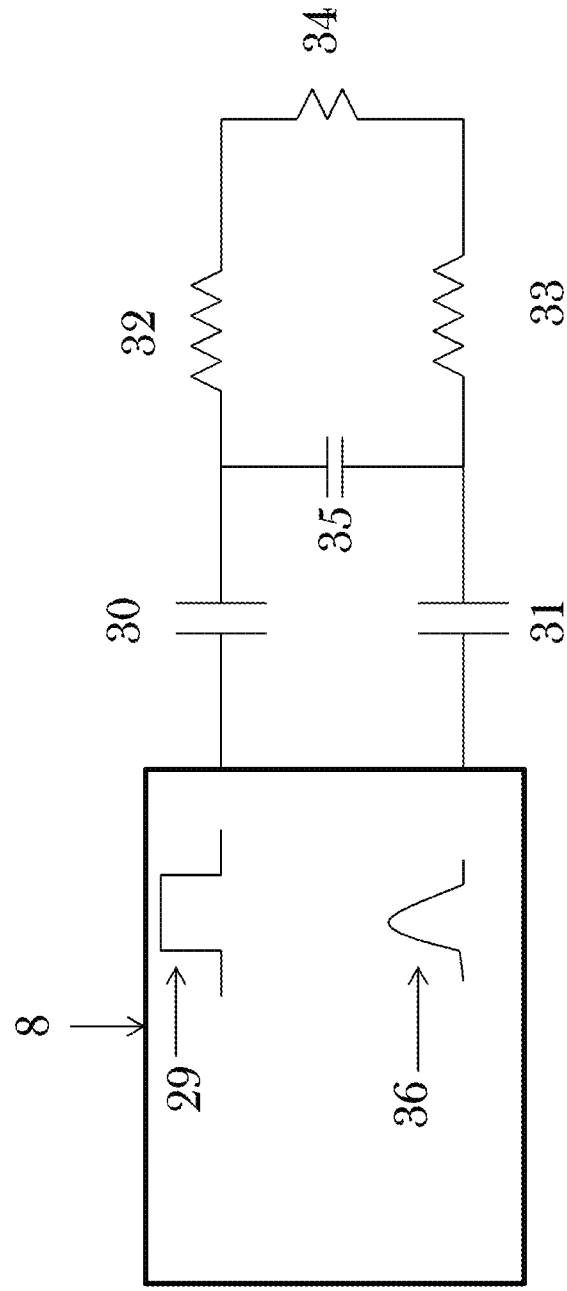
FIG. 12 is a schematic that illustrates the signal flow inside the Pod circuitry.

Referring to FIG. 12, it demonstrates what happens in the circuitry when the pads 20 capacitively couple with the sensor lines 6. In order to capacitively couple, it is necessary to have the Pod 8, and it sends an input analog signal, a square wave 29. The rising edge of the signal 29 is most important. The coupling capacitors 30, 31 are the pads 20 which sit inside the pod circuitry; both of them can be perceived as one coupling capacitor. The Pod 8 makes contact through a capacitor 30 which couples into the sensor line 6, which has a resistance 32. Then, the signal 29 travels to the resistance of the urine line 34 which is very small. The signal 29 flows into the other sensor line which has a resistance 33, then back into the coupling 31, and, finally, we get a signal back 36. This output signal 36 which comes back is a small signal. With the amplitude and the width of that signal 36, the elements present in the circuit 30-34 can be measured/determined. In the preferred embodiment, in this example, we have five elements. If everything else is equal, one will be able to measure the resistances 32, 33. It is important to measure 32, 33 while it is known that the resistive value of 34 is quite small; it's 34 almost like a short. The shorter the distance between the sensor line 6 and the pad 20, the lower the resistance, and the bigger the distance between them, the higher the resistance. Depending on where the urine line ends, that is the most critical point of measurement. It is important to accurately measure 32, 33, and the following paragraphs will explain just how we do that. Points 30, 31, which are the coupling capacitances, tend to change because every time you clip the Pod 8 onto the diaper 5, you are not in a perfect position. For example, sometimes it 8 can be in and out a little bit, or left and right, depending on how much pressure you apply to the Pod 8 upon initial insertion.

Figure 13:
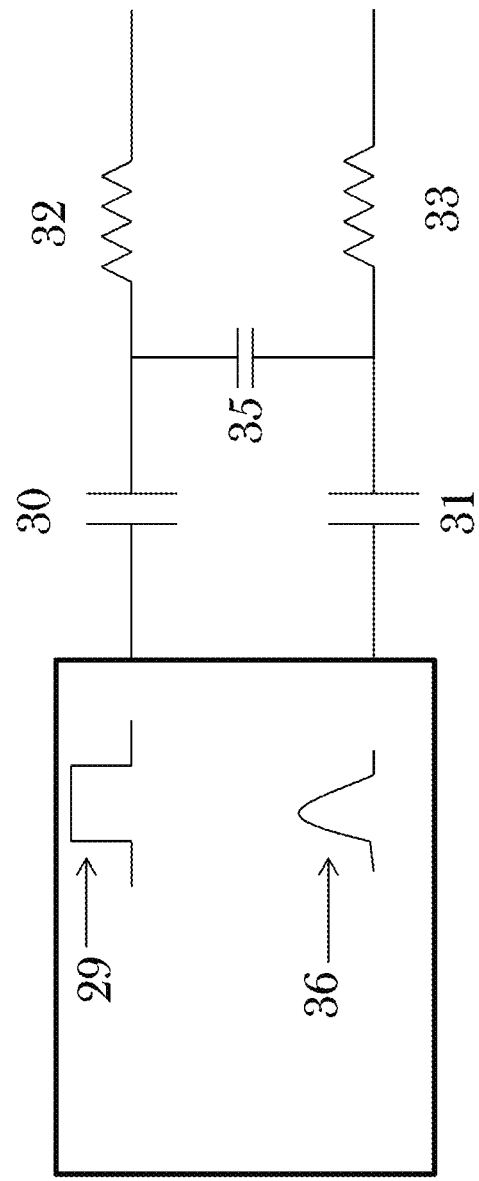
FIG. 13 is a schematic that demonstrates the signal flow upon initial insertion of the Pod into the diaper.

FIG. 13 depicts what happens upon initial insertion of the Pod 8 into the brief 5. Upon the initial insertion, the Pod 8 sends a signal as a square wave 29. We have a coupling capacitance 30, 31, a resistance, and there's a very small capacitance 35 between the two very long lines. In the preferred embodiment, in this example, if there's no urine present, then the resistive values of 32, 33 make no difference. The major effect will be from the capacitive values of 30, 31. There is a little bit of capacitance 35 in the middle as stated earlier. When the signal comes back 36, this output signal 36 can now be used to measure the unknown capacitive values of 30, 31. Every time the Pod 8 is placed on a new brief 5, one can measure 30, 31 because there is no urine. Hence, the resistances 32, 33 don't matter since the circuit is not closed due to the absence of urine. This measurement of 30, 31 will be known as a baseline measurement.

Figure 14:
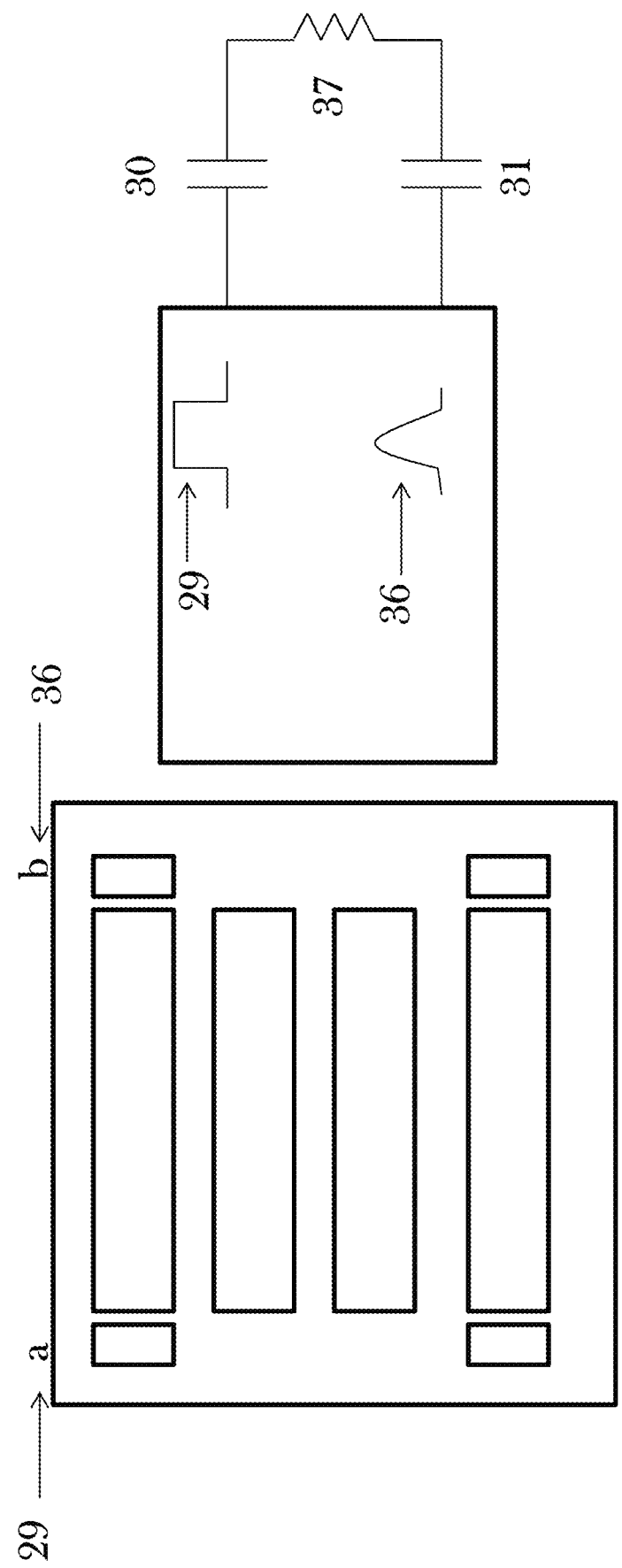
FIG. 14 is a schematic that shows how to measure the full resistivity of the diaper.

FIG. 14 illustrates how one can measure the resistive values of 32, 33. In order to know the values of 32, 33, it is essential to know the actual resistance of the diaper 37. The resistance of the carbon resistive lines can vary approximately 20% from diaper to diaper. Sometimes, in one of these lines, we have two pads 20 (capacitive coupling) on the PCB 19 in the preferred embodiment, which are separated from the big pad. A signal is sent between a 29 and b 36, and the resistance between these two capacitors 30, 31 is measured, and, in turn, that gives the resistivity of the full line 37. The resistivity of that line 37 is used to adjust the output 36. Furthermore, the baseline measurement of the capacitance 30, 31 is used as an input into measuring the actual resistance. Again, the baseline measurement is when there is no presence of urine. Between this circuit, a 29 and b 36 is basically the Pod sending a signal 29, a capacitive coupling 30, a resistance 37, a capacitive coupling 31, and a return signal 36. Usually, the carbon resistive lines 6 are very close to each other in the preferred embodiment and the capacitive coupling is very large compared to the resistance 37.

Figure 15:
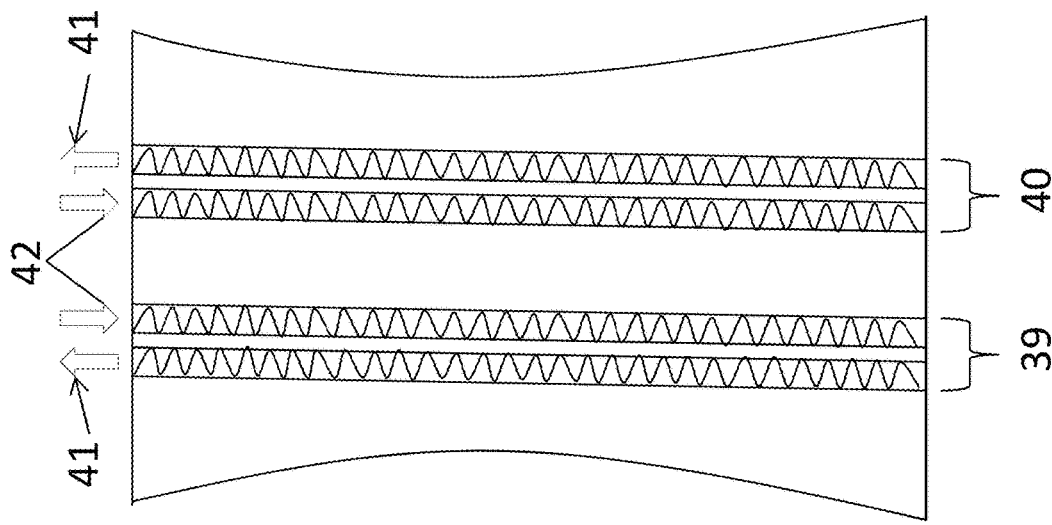
FIG. 15 depicts another possible embodiment that can contain more than two sets of carbon lines.

FIG. 15 shows that there can be two sets of two carbon lines 39, 40 in another embodiment. The carbon lines 39, 40, which are basically the sensor strips, are placed along the length of the diaper printed on the plastic film or the impermeable layer. In the first set of sesnor lines 39, the first carbon line is what we sense from the diaper ("Sense"). "Sense" 41 will be an output signal which we receive from the diaper. The second carbon line is what we push or drive into the diaper ("Drive"). Hence, "Drive" 42 will be an input signal or pulse we send into the diaper. In contrast to the first set of lines, the order is reversed in the second set of lines. Here, the first line is the input or "Drive" 42, and the second line is the output or "Sense" 41.

Figure 16:
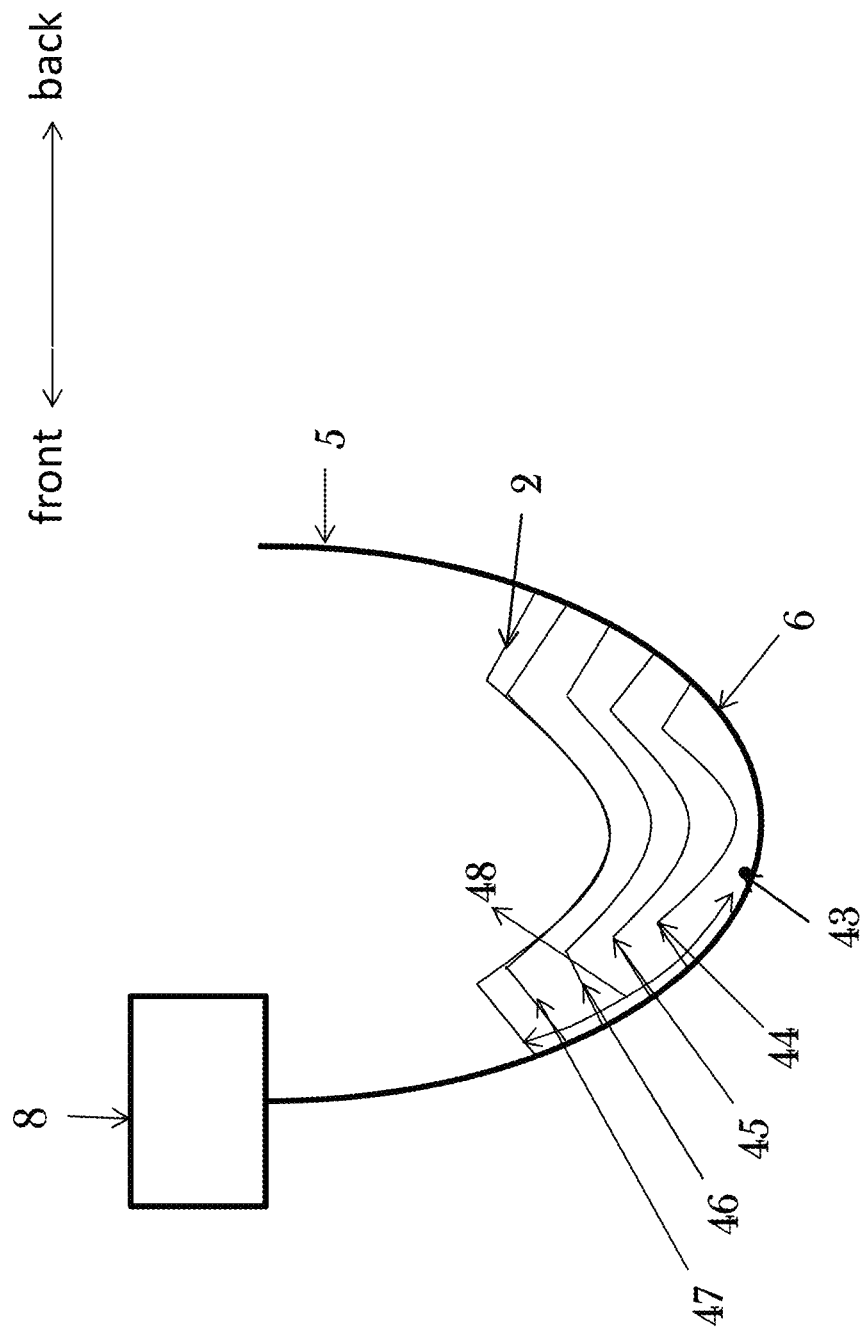
FIG. 16 is a side-view that illustrates another possible embodiment wherein a method is used to create a conductivity baseline.

Referring to FIG. 16, it shows another embodiment of the invention wherein a method is used to create a baseline of conductivity. Essentially when a resident urinates, conductivity is at the lowest and eventually increases with each urination event. In the preferred embodiment, the Pod 8 does not make physical contact with the sensor lines 6 due to the nonwoven layers present on each side of the diaper 5. Instead, the Pod 8 is close enough to the carbon-resistive sensor lines 6 and makes capacitive contact with them. An A.C. signal is sent to determine the resistance between two points: the Pod 8 and the urine line of contact. As the diaper 5 becomes saturated, resistance decreases while conductivity increases. Finally, the Pod 8 will determine a threshold of diaper saturation to send an alert to the caregiver for a diaper change before a leak becomes imminent. FIG. 16 is an example of another embodiment wherein a new method to perform the above task is taken into consideration. In this embodiment, a person urinates 20 ounces in order to consider the diaper to be fully saturated at point 47. Normally, an individual does not urinate 20 ounces in one millisecond. For instance, it takes him/her approximately 30 seconds to urinate 20 ounces. Given this scenario, the resident urinates the first two ounces in approximately one second. When these two ounces of liquid make contact with the diaper 5 at point 43, this point 43 will be used to create a baseline of conductivity. In this way, point 43 will become the basis or baseline to measure the distance from here 43 to the next point of urination 44. Upon each urination event, the direction of the liquid 48 will go further out and expand in both directions from the baseline point 43. In comparison to the preferred embodiment, this baseline method provides a means for measuring the resistance between a smaller area, from baseline 43 to the next urination event 44, thus, allowing for less sensitivity to variation in conductivity of the sensing lines. This, in turn, provides for better and more accurate saturation results.

Figure 17:
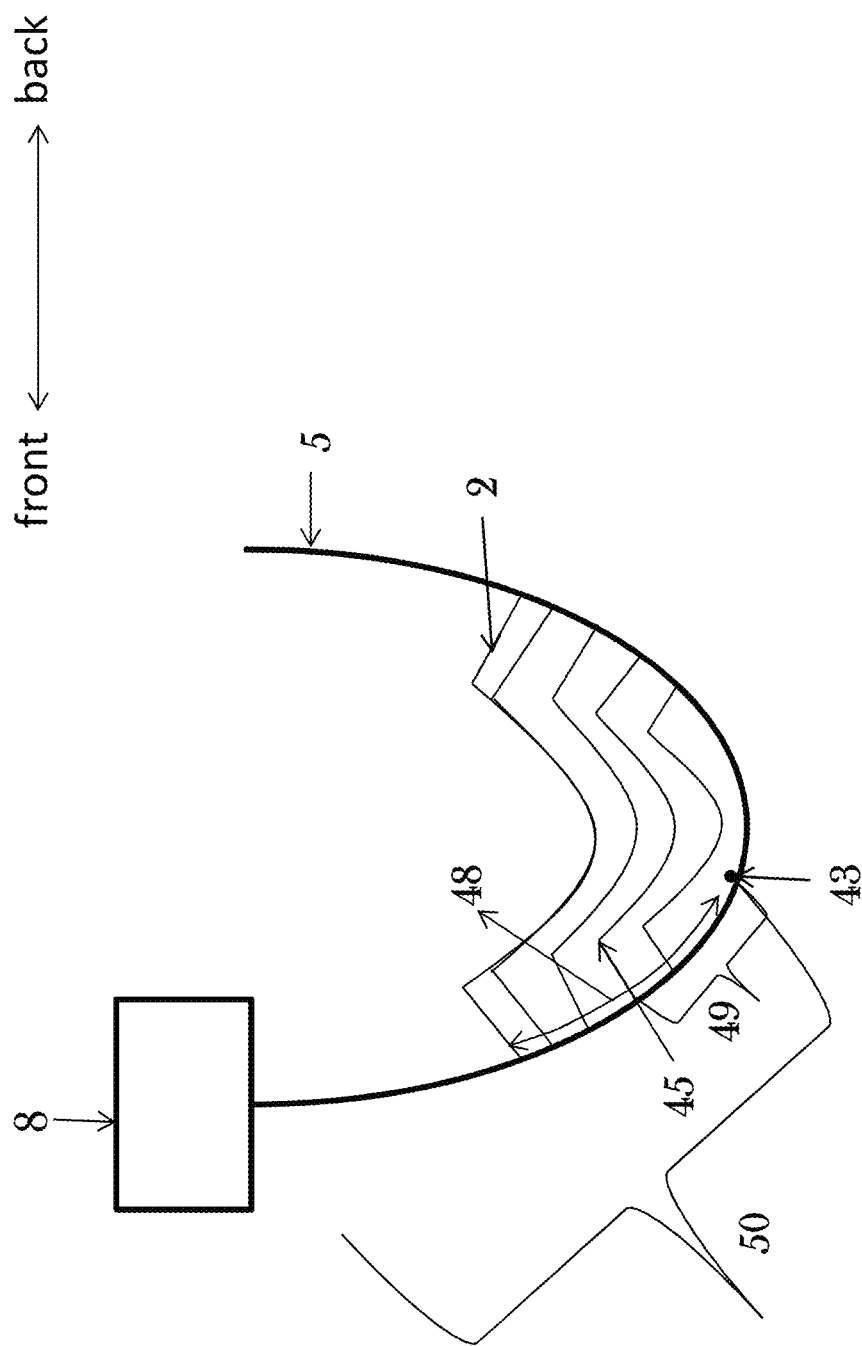
FIG. 17 is a side-view that demonstrates the creation of a baseline point in another possible embodiment of urination events in the sitting position.

FIG. 17 illustrates the creation of a baseline conductivity point in another embodiment wherein a resident urinates while sitting down. In this embodiment, when the first two ounces of urine make contact with the diaper 5, a baseline point 43 is established as opposed to the preferred embodiment. This first urine is very small and makes a close contact with the multiple sensor lines. From this baseline point 43 onwards, it will be determined as to how big the urine spot became. n this sitting posture, when the resident micturates, the fluid 48 will expand further out and go upwards due to the fibers present in the diaper 5. Since the printing process of the sensor lines is not always perfect, it is not possible to know the resistivity of these lines, and, hence, it varies. For example, the resistivity of the sensor lines can vary by 10% or even by 20%; likewise, the baseline urine point 43 may also vary by 10% or by 20%. All of this can lead to a misjudgment on the amount of diaper saturation. In the primary embodiment, the resistivity of the sensor lines must be known in order to measure the distance between the urine line of contact and the Pod 8. Even if the sensor line printing is off by 10-20%, the distance 49 that is being measured in this embodiment, that is from baseline 43 to the next saturation point 45, is relatively smaller in comparison to the larger distance 50 that is being measured in the preferred embodiment. In this embodiment, only a small change in conductivity is being measured, which is only 10% of the smaller distance 49. This is in stark contrast to the principle embodiment in which 10% of the overall larger distance 50 is being measured, from the urine line of contact to the Pod 8 itself. By using this approach, the resistance of the lines through the urine will not be measured. Instead, the distance between the lines will be known by determining the difference of the resistance between two points: where the first urine spot hit, and where it finally landed. Hence, the establishment of a baseline 43 makes the system less susceptible to changes in the resistance of the conductivity.

Figure 18:
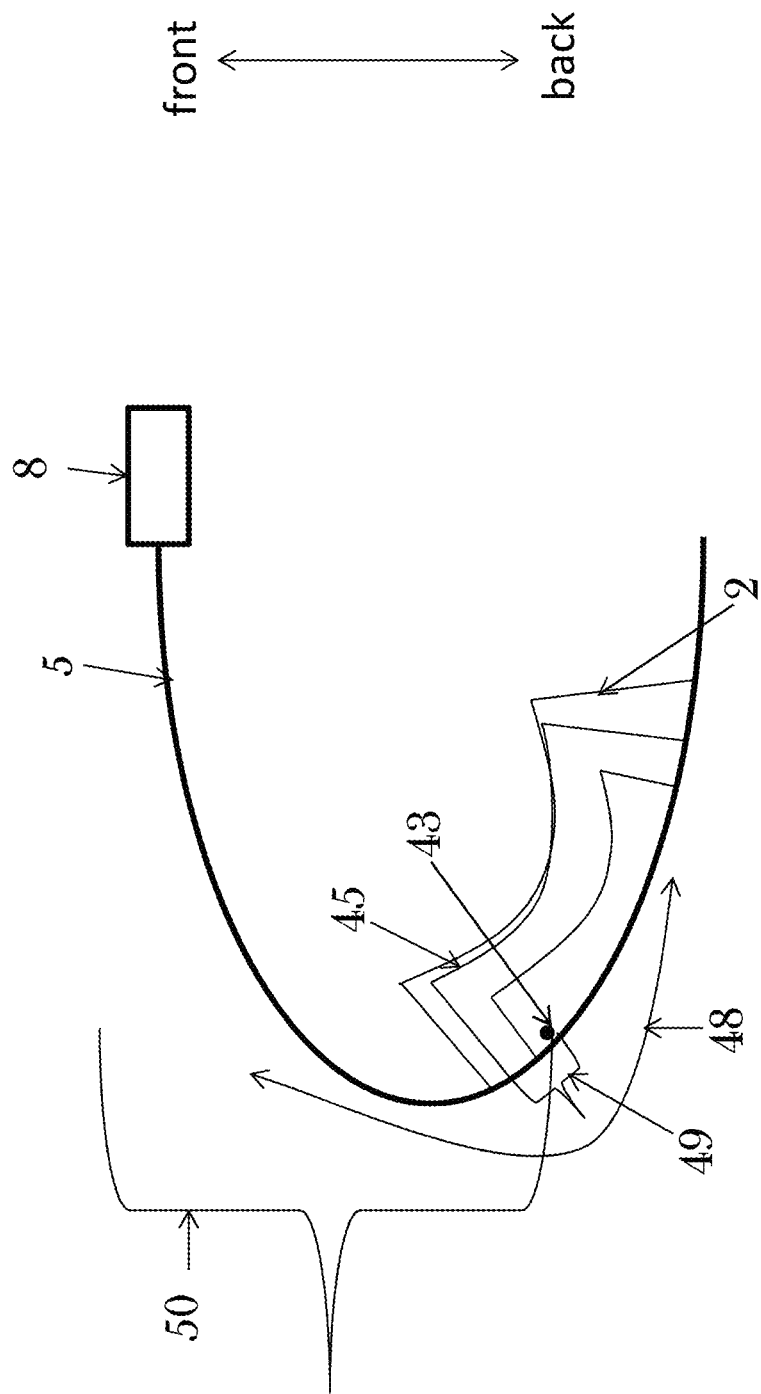
FIG. 18 is the left side-view that shows the creation of a baseline point in another possible embodiment of urination events in the lying down posture.

FIG. 18 demonstrates the creation of a baseline conductivity point in another embodiment wherein a resident undergoes urination events in the lying down position. A capacitively-coupled Pod 8 depends on many variables including but not limited to body positioning which, in turn, affects the system's output voltages. In this embodiment, the first point of fluid contact marks a baseline point 43. Here, in the lying down posture, the fluid 48 will go further down and expand on both sides of the baseline point 43. The distance from baseline 43 to the next wetness event 45 is measured as the difference from the first point of urination. In other words, the first point of urine contact is called "the baseline point." This method is more reliable as opposed to the one in the preferred embodiment which measures a much larger distance 50, from the point of urine contact to the Pod 8 itself, because it makes the system more resilient to changes in the environment. Moreover, the baseline method is well-grounded because it uses the first urine as a baseline in order to decide the difference between that and when the diaper saturation is achieved. All this, in turn, provides more precise saturation data results.

Referring to FIG. 18 B, the graph represents a comparison of conductivity vs. time of urination events in different positions, but with regards to the creation of a baseline as described in the previous paragraphs. This illustration allows one to vividly see what is happening with each urination event in each of the three different postures: sitting 65, lying down 66, and lying sideways 67. Essentially when a resident urinates, conductivity is at the lowest and eventually increases with each urination event. In this graph, it is illustrated that when the first two ounces of urine make contact with the diaper 5, a baseline point 64 is established as opposed to the preferred embodiment. This point 64 becomes the basis or baseline for measuring the distance from here to the next point of urination. It can be seen that the first time the resident urinates 5 ounces at point 13, conductivity is lowest in the lying down position 66, highest in the sideways position 67, and in-between in the normal, sitting posture 65. This pattern continues with each urination event and one can see a rise in conductivity. From this baseline point 64 onwards, it will be determined as to how big the urine spot became. In comparison to the preferred embodiment, this baseline method provides a means to measure the resistance between a smaller area, from baseline 64 to the next urination event, thus, allowing for less sensitivity to variation in conductivity of the sensing lines. This, in turn, provides for better and more accurate saturation results than the preferred embodiment method. By using this approach, the resistance of the lines through the urine will not be measured. Instead, the distance between the lines will be known by determining the difference of the resistance between two points: where the first urine spot hit, and where it finally landed. Hence, the establishment of a baseline 64 makes the system less susceptible to changes in the resistance of the conductivity.

Figure 19:
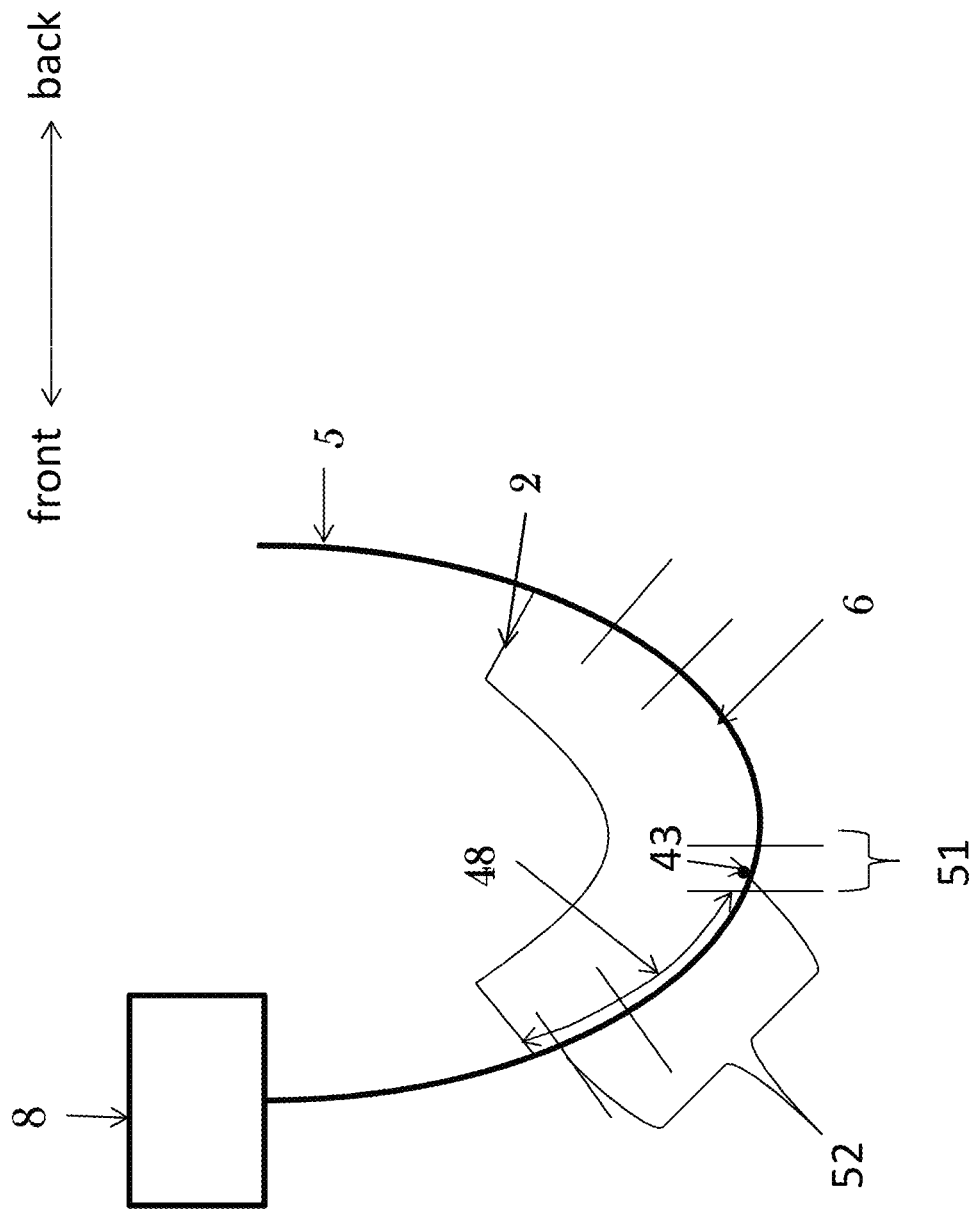
FIG. 19 is a side-view that shows the use of different frequencies for urine detection.

Referring to FIG. 19, upon the first instance of urination a baseline is formed at point 43. This approach requires using two different frequencies: a frequency to determine whether or not a resident has urinated 51, and another frequency to determine how big the urine became 52. First, a particular, lower frequency 51 is used that gives a higher difference in the output upon the first instance of urination. This is done to determine that the urination actually did occur. After that, a different frequency 52 is used to determine how much the urine expanded in the diaper in order to determine the change of resistance, and to say whether or not the diaper 5 is saturated enough to require changing.

Figure 20:
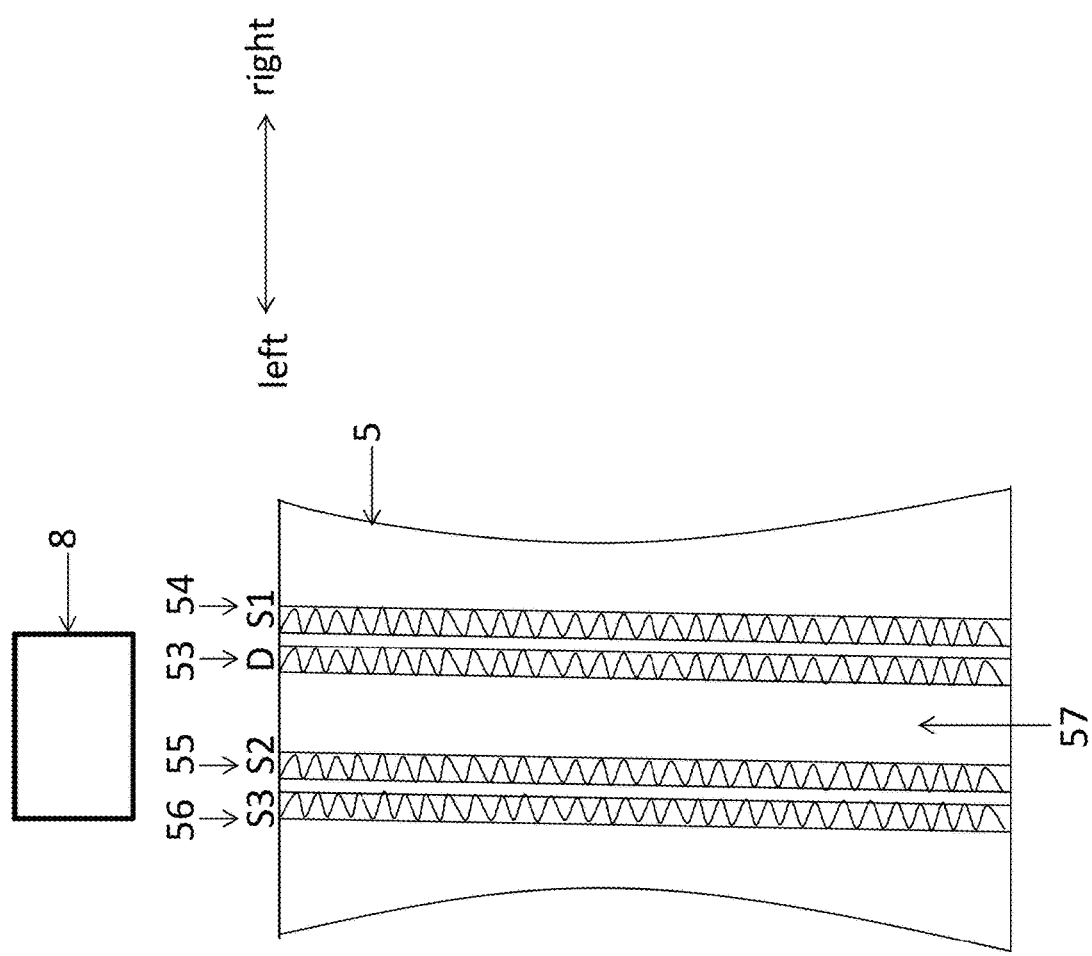
FIG. 20 is a top-view that illustrates the drive and sense lines.

FIG. 20 shows a top-view illustration of two sets of carbon lines 53-56 in another embodiment. In the set of lines on the right-side of the illustration, one line 53 is used for Drive, and another line 54 is used for Sense 1. In the set of lines on the left-side of the illustration, one line 55 is used for Sense 2, and another line 56 is used for Sense 3. In between these lines, there is a space 57 which can be used to place, for example, a wetness detector as a backup that makes use of chemicals to change the color upon detection of urine. In the current invention, signals are going from the Pod 8 and coming back to it. The Pod 8 sends a signal down through a Drive line 53,. The signal travels back and forth between the Pod 8 and the Drive line 53 in order to confirm the Pod 8 is correctly connected to the diaper 5. If the signal between the Pod 8 and the Drive line 53 is interrupted, it means the connection has been lost between the Pod 8 and the diaper 5. Sense lines deliver the signals back to the Pod 8._Using the Pod 8 as a reference point, the Drive line 53 is the output (what the Pod 8 is sending out) and the Sense lines 54, 55, 56 are the input (what is coming back to the Pod 8 or what it is sensing). Since the motion of a person will cause his/her body to get closer to or further away from the sensor lines, it will have an effect on the resistance of conductivity and the signal that comes back. As the body gets closer to the lines, it will steal the signal away from these lines. Hence, one way to make the signal more immune to the body is to do the following calculations: (Sense 1−Sense 2) or (Sense 1/Sense 2). Sense 2 55 can also be represented as the combination of Sense 2 and Sense 3 lines 55, 56 (Sense 2=Sense 2+Sense 3) because they get far less signals since they are further away from the Drive line 53. Combining the two sense lines gives a sum of two signals. With this in mind, the above formula that is used to make the signal more immune to the body can now be re-written as (Sense 1−(Sense 2+Sense 3) or (Sense 1/(Sense 2+Sense 3)), wherein the value of Sense 2 is substituted with (Sense 2+Sense 3). The reason why the signal is more immune to the body is because the capacitive coupling of the body stealing these signals will be equivalent or the same percentage from each one of the sense lines. If there was just one sense line, the amount of signal coming back will vary, not just on the urine, but also on the positioning of the body. If there is a second sense line further away, like in this illustration, the difference in the signal between the closer and further sense lines (Sense 1−(Sense 2+Sense 3)), will not depend on the body. This is because the body will steal away the same percentage; the difference or the quotient of the two sense signals will roughly be the same, no matter how close the body is to the sense lines.

Figure 21:
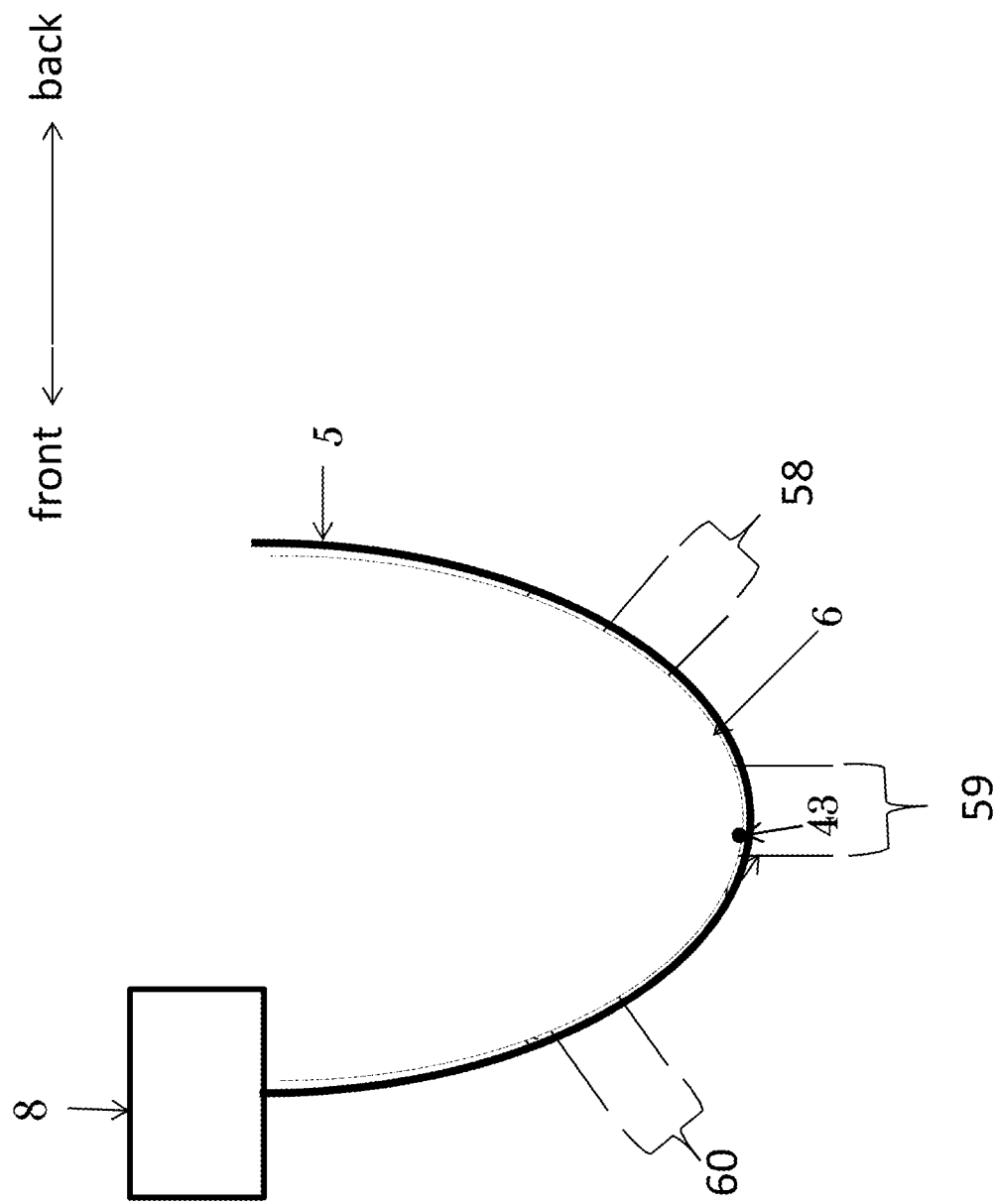
FIG. 21 is a side-view that depicts the use of different frequencies to indicate the presence of urine relative to Pod distance.

Referring to FIG. 21, in the manufacturing of the diaper, the carbon lines 6 are printed on the plastic film or the impermeable layer along the length of the diaper 5. When a Pod 8 is not installed on the diaper 5, there is no signal because a connection has not been established. Initially, when the Pod 8 is placed on a diaper 5, even if there is no urination event, a small signal comes back because there is a coupling effect between the lines 6, between the Drive 53 and the Sense lines 54-56 as described in FIG. 20. This small signal is used to detect whether or not the Pod 8 is connected to the diaper 5. When there is a first instance of urination, it marks a baseline point 43. The baseline indicates the signal strength that comes back from each one of the Sense lines 54-56 (FIG. 20). This baseline point 43 is used to measure the distance between the first urination occurrence and the next in order to determine whether the diaper is saturated enough or not to require changing. Depending on where a resident urinates, a different frequency 58, 59, 60 is used in order to give a better signal to noise ratio for liquid detection. The frequency can be changed because it is being sent through the Drive line 53, and the signal that comes back is a smaller signal. In the illustration, a higher frequency 60 is represented to detect urine that is closer to the Pod 8, while a lower frequency 59 detects liquid that is further away from the Pod 8. There is also a lower frequency in area 58 as compared to area 60, because this area is further away from the Pod 8.

Figure 22:
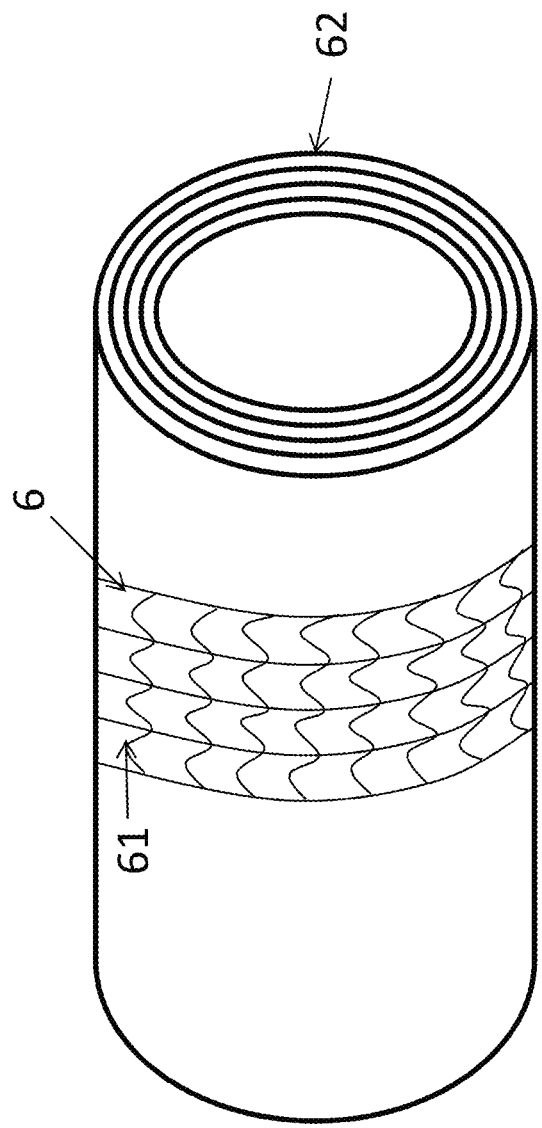
FIG. 22 is a top-view of a roll of diaper sheets that shows occurrence of bumps.

FIG. 22 demonstrates the top view of a roll 62 of an impermeable layer of diaper sheets wherein bumps 61 are present on the roll 62. In diaper manufacturing mechanics, three sheets of nonwoven fabric are formed from plastic resin using a meltblown process. These sheets are produced as a wide roll known as a "web" 62 which is then cut to the appropriate width for use in diapers. The thick web roll 62 is in long strips and because its thickness is quite significant, this causes the formation of bumps 61 on it. These bumps 61 not only lead to difficulty in manufacturing, but also cause the plastic sheet material of the diaper to stretch. In turn, this causes variations in the resistance which is highly undesirable.

Figure 23:
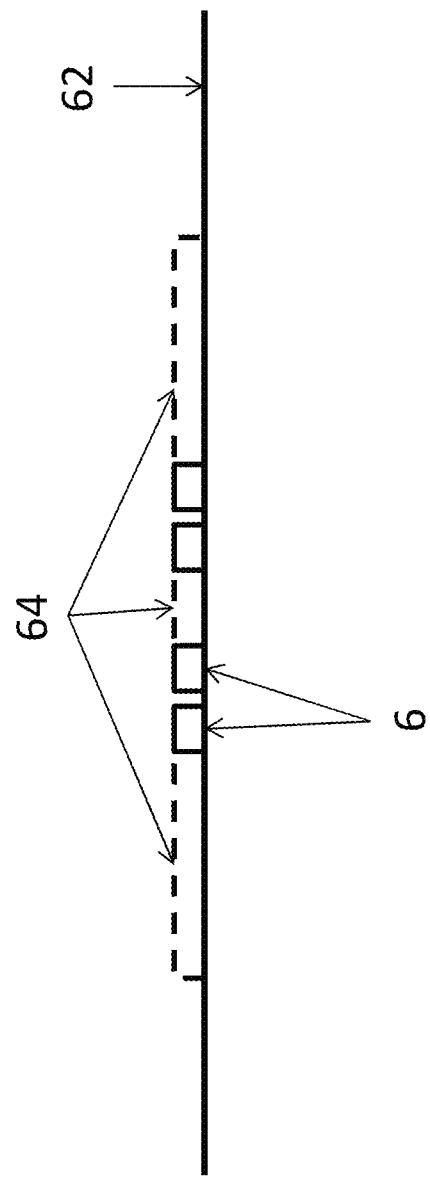
FIG. 23 is a cross-sectional view of a roll of diaper sheets.

FIG. 23 depicts a cross-sectional view of a big roll of diaper sheet 62 that is approximately 40 μm long. For the sake of simplicity, the carbon lines 6 have been drawn as boxes in this illustration. Due to the printing of the carbon lines 6 on the plastic sheet, it creates bumps 61 on the roll 62 because of the thickness of the printing. For example, the thickness of the plastic sheet is about 12 μm, and the printing thickness is about 5 μm; hence, the printing causes bumps 61 to occur, and that, in turn stretches the plastic. The stretching further affects the resistance of these lines and also causes problems in rolling and re-rolling, and so on. In order to effectively counteract the problem of bump appearance 61 on the roll 62 due to its great thickness, adding an additional layer of polymer 64 can prove to be a useful solution. The additional polymer layer 64 may be printed in various locations on the sides of the carbon lines 6 and even in-between them. This extra layer 64 will be of equivalent thickness to the carbon ink in order to equalize them upon rolling.

The invention claimed is:

1. A method for detecting an amount of wetness of an absorbent article, wherein the absorbent article is provided with at least two conductive lines along its length, the method comprising:
   detecting, with a first frequency, an initial liquid touching line that connects two of the conductive lines by a sharp rise on the first frequency;
   detecting, with a second frequency, an final liquid touching line that connects the two of the conductive lines by a rise on the second frequency; and
   determining the amount of wetness of the absorbent article by a difference between the initial and final liquid touching lines.

2. A method for detecting an amount of wetness of an absorbent article, wherein the absorbent article is provided with at least two conductive lines along its length, the method comprising:
   detecting, with a frequency, an initial liquid touching line that connects two of the conductive lines;
   detecting, with the frequency, an final liquid touching line that connects the two of the conductive lines; and
   determining the amount of wetness of the absorbent article by a difference between the initial and final liquid touching lines with the rise of the frequency.

3. A method for detecting an amount of wetness of an absorbent article, wherein the absorbent article is provided with at least two conductive lines along its length, the method comprising: using multiple frequencies, the multiple frequencies being different from each other, and wherein one of the multiple frequencies with highest rise range is used to determine the amount of wetness of the absorbent article.

4. A system for detecting an amount of wetness of an absorbent article, wherein the absorbent article is provided with at least two conductive lines along its length, the system comprising:
   a detector configured to detect, with a first frequency, an initial liquid touching line that connects two of the conductive lines by a sharp rise on the first frequency and to detect, with a second frequency, an final liquid touching line that connects the two of the conductive lines by a rise on the second frequency; and
   a wetness determination unit configured to determine the amount of wetness of the absorbent article by a difference between the initial and final liquid touching lines.

5. A system for detecting an amount of wetness of an absorbent article, wherein the absorbent article is provided with at least two conductive lines along its length, the system comprising:
   a detector configured to detect, with a frequency, an initial liquid touching line that connects two of the conductive lines and to detect, with the frequency, an final liquid touching line that connects the two of the conductive lines; and
   a wetness determination unit configured to determine the amount of wetness of the absorbent article by a difference between the initial and final liquid touching lines with the rise of the frequency.

6. A system for detecting an amount of wetness of an absorbent article, wherein the absorbent article is provided with at least two conductive lines along its length, the system comprising: a detector configured to detect, with multiple frequencies, a final liquid touching line that connects two of the conductive lines, the multiple frequencies being different from each other, and a wetness determination unit configured to use the final liquid touching line detected from one of the multiple frequencies with highest rise range to determine the amount of wetness of the absorbent article.

7. A method for detecting an amount of wetness of an absorbent article, wherein the absorbent article is provided with at least two conductive lines along its length, the method comprising:
   detecting, with a first signal, an initial liquid touching line that connects two of the conductive lines by a sharp rise on the first signal;
   detecting, with a second signal, an final liquid touching line that connects the two of the conductive lines by a rise on the second signal; and
   determining the amount of wetness of the absorbent article by a difference between the initial and final liquid touching lines.

8. The method as claimed in claim 7, wherein multiple second signals are used to detect the final liquid touching line, the multiple second signals being different from each other, and wherein the final liquid touching line detected from one of the multiple second signals with highest rise range is used to determine the amount of wetness of the absorbent article.

9. A system for detecting a saturation or an amount of wetness of an absorbent article, the system comprising:
   an orientation detection unit configured to detect an orientation of the absorbent article;
   a wetness detection unit configured to detect the amount of wetness of the absorbent article based on at least two conductive lines and the measurement difference between an initial urination and a final spread of urine in the absorbent article; and
   a determination unit configured to determine the saturation or the amount of wetness of the absorbent article based on both the orientation and the amount of wetness of the absorbent article as detected.

10. The system as claimed in claim 9, wherein the determination unit comprises:
   a saturation threshold determination unit configured to determine a threshold of saturation based on the detected orientation of the absorbent article; and
   a comparator configured to compare the detected amount of wetness of the absorbent article to the determined threshold of saturation.

11. A wetness detection device with an orientation sensing and alerting function, comprising:
   an orientation sensing unit configured to continuously sense an orientation of a user wearing the wetness detection device; and
   a transmitter configured to transmit an alert when the orientation sensing unit fails to sense a change in orientation of the user for a predetermined period.

12. A method for detecting an amount of wetness of an absorbent article, wherein the absorbent article is provided with at least two conductive lines along its length, the method comprising:
   detecting an initial liquid touching line that connects two of the conductive lines;
   detecting an final liquid touching line that connects the two of the conductive lines; and
   determining the amount of wetness of the absorbent article by a difference between the initial and final liquid touching lines.

13. A method for monitoring a wearer of an absorbent article, wherein the absorbent article is provided with at least two conductive lines along its length, and wherein an attachment device equiped with an orientation detector is coupled to the absorbent article, the method comprises: checking the movement of the body of the wearer of the absorbent article with the orientation detector, and sending alert if the wearer does not move in a specified number of time.

* * * * *